United States Patent
Fukuda et al.

(10) Patent No.: US 9,873,676 B2
(45) Date of Patent: Jan. 23, 2018

(54) ISOCYANURATE COMPOSITION

(71) Applicant: MITSUI CHEMICALS, INC., Tokyo (JP)

(72) Inventors: Kazuyuki Fukuda, Ichihara (JP); Hideaki Otsuka, Chiba (JP); Tsutomu Yoshida, Chigasaki (JP); Tatsuya Nakashima, Takarazuka (JP); Toshiaki Moriya, Sagamihara (JP); Shirou Honma, Yokohama (JP)

(73) Assignee: MITSUI CHEMICALS, INC., Tokyo (JP)

( * ) Notice: Subject to any disclaimer, the term of this patent is extended or adjusted under 35 U.S.C. 154(b) by 0 days.

(21) Appl. No.: 15/123,200

(22) PCT Filed: Mar. 3, 2015

(86) PCT No.: PCT/JP2015/056253
§ 371 (c)(1),
(2) Date: Sep. 1, 2016

(87) PCT Pub. No.: WO2015/133494
PCT Pub. Date: Sep. 11, 2015

(65) Prior Publication Data
US 2017/0073317 A1   Mar. 16, 2017

(30) Foreign Application Priority Data

Mar. 4, 2014 (JP) ................. 2014-041952
Mar. 4, 2014 (JP) ................. 2014-041957

(51) Int. Cl.
| | | |
|---|---|---|
| *C07D 251/32* | (2006.01) | |
| *C08G 18/76* | (2006.01) | |
| *C08G 18/02* | (2006.01) | |
| *C08G 18/09* | (2006.01) | |
| *C08G 18/18* | (2006.01) | |
| *B32B 7/12* | (2006.01) | |
| *B32B 15/085* | (2006.01) | |
| *B32B 15/20* | (2006.01) | |
| *B32B 27/32* | (2006.01) | |
| *B32B 37/12* | (2006.01) | |
| *C08G 18/12* | (2006.01) | |
| *C08G 18/30* | (2006.01) | |
| *C08G 18/38* | (2006.01) | |
| *C09J 7/02* | (2006.01) | |
| *C09J 175/04* | (2006.01) | |

(52) U.S. Cl.
CPC ............. *C07D 251/32* (2013.01); *B32B 7/12* (2013.01); *B32B 15/085* (2013.01); *B32B 15/20* (2013.01); *B32B 27/32* (2013.01); *B32B 37/12* (2013.01); *C08G 18/022* (2013.01); *C08G 18/092* (2013.01); *C08G 18/12* (2013.01); *C08G 18/1875* (2013.01); *C08G 18/30* (2013.01); *C08G 18/3885* (2013.01); *C08G 18/7642* (2013.01); *C08G 18/7692* (2013.01); *C09J 7/0296* (2013.01); *C09J 175/04* (2013.01); *B32B 2037/1246* (2013.01); *B32B 2255/06* (2013.01); *B32B 2255/10* (2013.01); *B32B 2255/26* (2013.01); *B32B 2311/24* (2013.01); *B32B 2323/10* (2013.01); *B32B 2553/00* (2013.01)

(58) Field of Classification Search
CPC ............................. C07D 251/32; C08G 18/022
See application file for complete search history.

(56) References Cited

U.S. PATENT DOCUMENTS

| | | | |
|---|---|---|---|
| 3,920,644 | A | 11/1975 | Nishibata |
| 4,864,025 | A | 9/1989 | Robin |
| 2013/0116357 | A1 | 5/2013 | Laas |
| 2013/0158145 | A1 | 6/2013 | Laas |

FOREIGN PATENT DOCUMENTS

| | | |
|---|---|---|
| CN | 102134255 A | 7/2011 |
| CN | 102167925 A | 8/2011 |
| JP | 50030843 A2 | 3/1975 |
| JP | 54138586 A2 | 10/1979 |
| JP | 31012677 A2 | 1/1986 |
| JP | 63145273 A2 | 6/1988 |
| JP | 10060082 A2 | 3/1998 |
| JP | 10319202 A2 | 12/1998 |
| JP | 2013531123 T2 | 8/2013 |
| JP | 2013532738 T2 | 8/2013 |
| WO | 2008065732 A1 | 6/2008 |
| WO | 2012010524 A1 | 1/2012 |

OTHER PUBLICATIONS

International Search Report dated Jun. 9, 2015 filed in PCT/JP2015/056253.
International Preliminary Report on Patentability dated Sep. 15, 2016 filed in PCT/JP2015/056253 total 11 pages.

*Primary Examiner* — Kahsay Habte
(74) *Attorney, Agent, or Firm* — Rankin, Hill & Clark LLP

(57) ABSTRACT

The isocyanate composition consists essentially of an isocyanurate derivative of 1,3-xylylenediisocyanate, the isocyanurate derivative is modified with aliphatic alcohol, and the modification amount of the aliphatic alcohol is 0.5 mass % or more and 15 mass % or less.

5 Claims, 2 Drawing Sheets

ISOCYANURATE COMPOSITION

TECHNICAL FIELD

The present invention relates to an isocyanurate composition, i.e., material of polyurethane resin.

BACKGROUND ART

Polyurethane resin is generally produced by reaction of polyisocyanate and an active hydrogen group-containing compound, and is widely used in various industrial fields as, for example, coatings, adhesives, and elastomers.

For polyisocyanate used in production of polyurethane resin, for example, xylylenediisocyanate (XDI) is known, and it has been proposed that xylylenediisocyanate is derived into an isocyanurate derivative to be used.

To be more specific, Patent Document 1 has proposed (ref: polyisocyanate A3 in Example) production of m-XDI allophanate polyisocyanate containing an isocyanurate group by, for example, after modifying m-XDI with benzylalcohol, allowing reaction in 2-ethyl-hexanol using a 50% concentration solution of zinc (II) 2-ethylhexanoate as a trimerization catalyst, and then adding orthophosphoric acid and terminating the reaction.

CITATION LIST

Patent Document

Patent Document 1: Japanese Unexamined Patent Application Publication (Translation of PCT Application) 2013-531123

SUMMARY OF THE INVENTION

Problem to be Solved by the Invention

However, the polyurethane resin produced from the polyisocyanate described in the above-described Patent Document 1 has insufficient weatherability.

Furthermore, further improvement in durability of polyurethane resin is demanded in various industrial fields.

An object of the present invention is to provide an isocyanurate composition that can produce a polyurethane resin having excellent weatherability and durability.

Means for Solving the Problem

An isocyanurate composition of the present invention consists essentially of an isocyanurate derivative of 1,3-xylylenediisocyanate, wherein the isocyanurate derivative is modified with aliphatic alcohol, and the modification amount of the aliphatic alcohol is 0.5 mass % or more and 15 mass % or less.

In the isocyanurate composition of the present invention, it is preferable that the modification amount of the aliphatic alcohol is 3.0 mass % or more and 7.0 mass % or less.

In the isocyanurate composition of the present invention, it is preferable that the aliphatic alcohol has carbon atoms of 4 or more and 20 or less.

In the isocyanurate composition of the present invention, it is preferable that the aliphatic alcohol is dihydric aliphatic alcohol.

Effect of the Invention

The isocyanurate composition of the present invention can produce polyurethane resin with excellent weatherability and durability.

DESCRIPTION OF EMBODIMENTS

Figure 1:
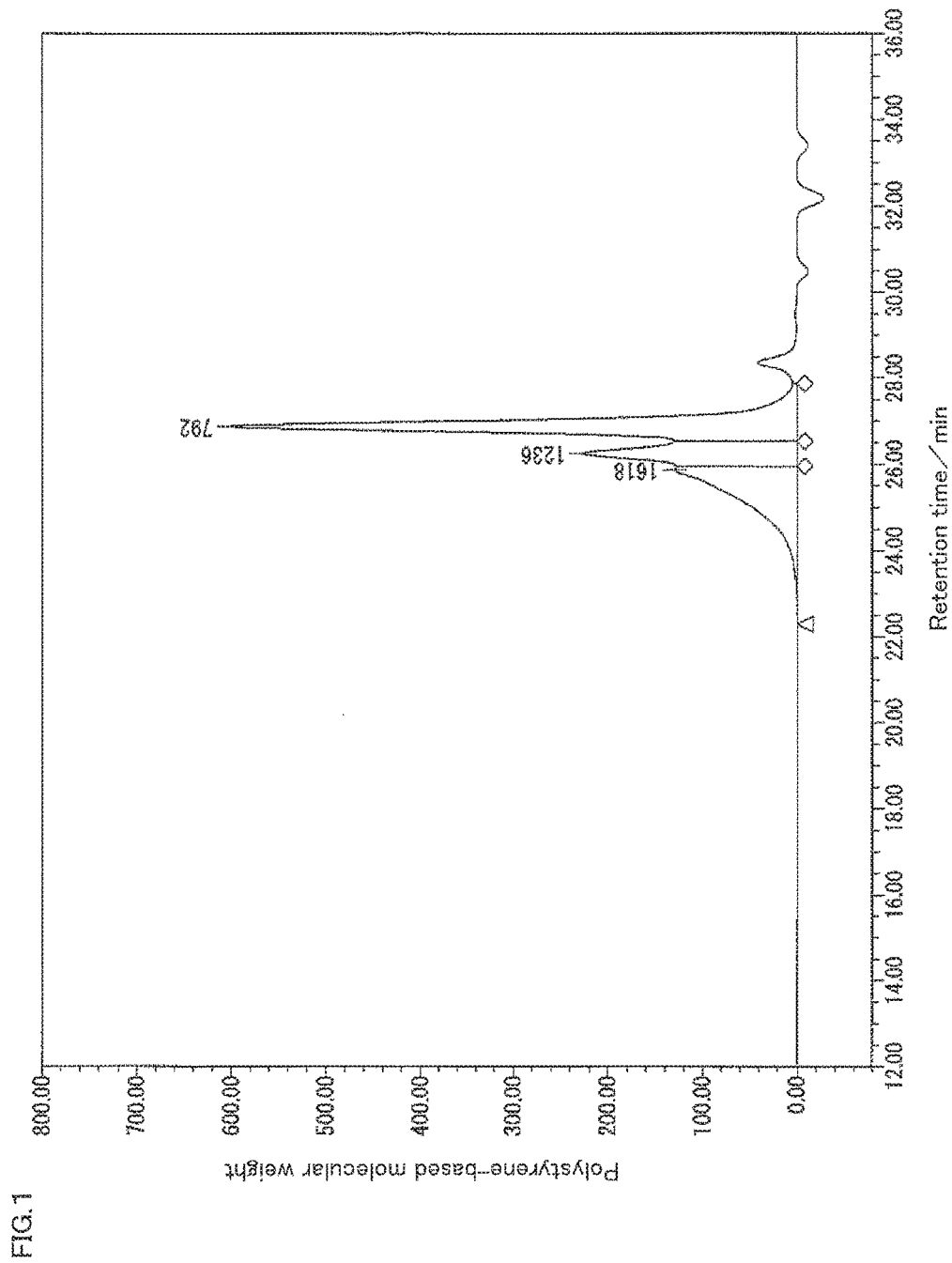
FIG. 1 is a gel permeation chromatogram of the isocyanurate composition of Example 4.

The isocyanurate composition of the present invention consists of an isocyanurate derivative of 1,3-xylylenediisocyanate (m-xylylenediisocyanate (m-XDI)). The isocyanurate composition of the present invention contains the isocyanurate derivative of 1,3-xylylenediisocyanate as the sole main component, but allows for inevitably included secondary ingredients (e.g., catalysts, promoters, and stabilizers blended in the production of isocyanurate derivative, iminooxadiazinedione derivative of 1,3-xylylenediisocyanate, 1,3-xylylenediisocyanate monomer, etc.) to be contained in the isocyanurate composition.

The isocyanurate composition of the present invention does not include isocyanurate derivative of 1,2- or 1,4-xylylenediisocyanate, and is composed only of the isocyanurate derivative of 1,3-xylylenediisocyanate.

The isocyanurate derivative of 1,3-xylylenediisocyanate is a trimer of 1,3-xylylenediisocyanate. The trimer includes symmetrical trimer, i.e., isocyanurate derivative, and an asymmetrical trimer, i.e., iminooxadiazinedione derivative, but the isocyanurate composition of the present invention consists essentially of the isocyanurate derivative of 1,3-xylylenediisocyanate, and the iminooxadiazinedione derivative of 1,3-xylylenediisocyanate may be contained, relative to a total amount of the isocyanurate composition, in an amount of, for example, 6 mass % or less, preferably 2 mass % or less, more preferably 1 mass % or less, still more preferably 0.5 mass % or less.

The isocyanurate derivative of 1,3-xylylenediisocyanate is produced by subjecting 1,3-xylylenediisocyanate to isocyanurate-forming reaction in the presence of an isocyanurate-forming catalyst.

In the present invention, the isocyanurate-forming catalyst is not particularly limited as long as it is a catalyst that activates isocyanurate formation, and examples thereof include tertiary amines such as triethylamine, tributylamine, triethylenediamine, and a secondary amine copolymer (e.g., polycondensate of secondary amines such as dialkylamine, and a monomer that is copolymerizable with secondary amines (e.g., phenol, formaldehyde, etc.)); mannich base such as 2-dimethylaminomethylphenol and 2,4,6-tris (dimethylaminomethyl) phenol; hydroxides of tetraalkylammoniums such as tetramethylammonium, tetraethylammonium, tetrabutylammonium, trimethylbenzylammonium, and tributylbenzylammonium, and organic weak acid salt thereof; hydroxides of trialkylhydroxyalkylammoniums such as trimethylhydroxypropylammonium (also called: N-(2-hydroxypropyl)-N,N,N-trimethylammonium), trimethylhydroxyethylammonium, triethylhydroxypropylammonium, and triethylhydroxyethylammonium, and organic weak acid salt thereof; metal salt (e.g., salt of alkali metal, magnesium salt, tin salt, zinc salt, lead salt, etc.) of alkylcarboxylic acids such as acetic acid, caproic acid, octylic acid, myristic acid, and naphthenic acid; metal chelate compounds of β-diketone such as aluminum acetylacetone and lithium acetylacetonate; Friedel-Crafts catalysts such as aluminum chloride and boron trifluoride; various organometallic compounds such as titaniumtetrabutyrate and tributylantimonyoxide; aminosilyl-group-containing compounds such as hexamethylsilazane; and harogen substituted organic phosphorus compounds such as tetrabutylphosphonium hydrogendifluoride.

These isocyanurate-forming catalysts may be used singly or in combination of two or more.

For the isocyanurate-forming catalyst, preferably, hydroxide of tetraalkylammonium and hydroxide of trialkylhydroxyalkylammonium are used, more preferably, hydroxide of tetraalkylammonium is used, even more preferably, hydroxide of trimethylbenzylammonium, and hydroxide of tetrabutylammonium are used.

When the above-described catalyst is used as the isocyanurate-forming catalyst, 1,3-xylylenediisocyanate can be subjected to isocyanurate formation at a particularly excellent reaction rate, and therefore excellent production efficiency can be achieved.

The mixing ratio of the isocyanurate-forming catalyst (active component 100% based) relative to 100 parts by mass of the 1,3-xylylenediisocyanate is, for example, 0.001 parts by mass (phr) or more, preferably 0.009 parts by mass (phr) or more, more preferably 0.015 parts by mass (phr) or more, and for example, 0.1 parts by mass (phr) or less, preferably 0.024 parts by mass (phr) or less, more preferably 0.021 parts by mass (phr) or less, still more preferably 0.018 parts by mass (phr) or less.

In this method, 1,3-xylylenediisocyanate is blended with the isocyanurate-forming catalyst at the above-described mixing ratio, and the mixture is heated to cause isocyanurate-forming reaction.

The reaction conditions for the isocyanurate-forming reaction are as follows: for example, under an atmosphere of inert gas such as nitrogen gas, normal pressure (atmospheric pressure), a reaction temperature (maximum temperature reached) of, for example, 20° C. or more, preferably more than 40° C., more preferably 45° C. or more, still more preferably 60° C. or more, particularly preferably 70° C. or more, and for example, 90° C. or less, preferably 80° C. or less, more preferably 75° C. or less. The reaction time is, for example, 30 minutes or more, preferably 60 minutes or more, more preferably 120 minutes or more, still more preferably 250 minutes or more, particularly preferably 350 minutes or more, for example, 720 minutes or less, preferably 600 minutes or less, more preferably 480 minutes or less, still more preferably 450 minutes or less.

The isocyanurate-forming catalyst can be blended at the charging stage of the isocyanurate-forming reaction (initial period), can be added during the isocyanurate-forming reaction, and the above-described mixing ratio is a total of the mixing ratio (charged ratio) of the isocyanurate-forming catalyst blended before the start of the isocyanurate-forming reaction (initial period) and the mixing ratio (added ratio) of the isocyanurate-forming catalyst added during the isocyanurate-forming reaction.

When the isocyanurate-forming catalyst is added at both of the charging stage and during reaction of the isocyanurate-forming reaction, the mixing ratio of the isocyanurate-forming catalyst (charged ratio) blended before the isocyanurate-forming reaction (initial period) relative to 100 parts by mass of 1,3-xylylenediisocyanate is, for example, 0.001 parts by mass (phr) or more, preferably 0.002 parts by mass (phr) or more, more preferably 0.003 parts by mass (phr) or more, and for example, 0.1 parts by mass (phr) or less, preferably 0.005 parts by mass (phr) or less, more preferably 0.004 parts by mass (phr) or less; and the mixing ratio of the isocyanurate-forming catalyst (added ratio) added during the isocyanurate-forming reaction relative to 100 parts by mass of 1,3-xylylenediisocyanate is, for example, 0.001 parts by mass (phr) or more, preferably 0.006 parts by mass (phr) or more, more preferably 0.012 parts by mass (phr) or more, and for example, 0.1 parts by mass (phr) or less, preferably 0.021 parts by mass (phr) or less, more preferably 0.018 parts by mass (phr) or less, still more preferably 0.015 parts by mass (phr) or less.

The ratio of the charged ratio to the added ratio (charged ratio/added ratio) of the isocyanurate-forming catalyst is, setting the total of the charged ratio and added ratio as 100, for example, 10/90 or more, preferably 15/85 or more, more preferably 20/80 or more, and for example, 90/10 or less, preferably 50/50 or less, more preferably 30/70 or less.

In the above-described reaction, to adjust the isocyanurate formation, for example, organic phosphite described in Japanese Unexamined Patent Publication No. Sho 61-129173 can be blended as a promoter.

Examples of the organic phosphite include aliphatic organic phosphite and aromatic organic phosphite.

Examples of the aliphatic organic phosphite include alkyl monophosphites such as triethyl phosphite, tributyl phosphite, tris (2-ethylhexyl) phosphite, tridecyl phosphite, trilauryl phosphite, tris (tridecyl) phosphite, and tristearyl phosphite; di, tri, or tetra phosphites derived from aliphatic polyhydric alcohols such as distearyl•pentaerythrityl•diphosphite, di•dodecyl•pentaerythritol•diphosphite, di•tridecyl•pentaerythritol•diphosphite, and tripentaerythritol•tri phosphite; and furthermore, alicyclic poly phosphites such as a hydrogenated bisphenol A phosphite polymer (molecular weight 2400 to 3000), and tris (2,3-dichloropropyl) phosphite. For aliphatic organic phosphite, preferably, alkyl monophosphites are used, more preferably, tridecyl phosphate is used.

Examples of the aromatic organic phosphite include aryl monophosphites such as triphenyl phosphite, tris (nonylphenyl) phosphite, tris (2,4-di-t-butylphenyl) phosphite, diphenyldecyl phosphite, and diphenyl (tridecyl) phosphite; di, tri, or tetra phosphite derived from aromatic polyhydric alcohol such as dinonylphenyl•pentaerythritol•diphosphite, tetraphenyl•tetra•tridecyl•pentaerythrityl•tetra phosphite, and tetraphenyl•dipropylene glycol•diphosphite; and furthermore, diphosphites derived from bisphenol compounds such as di•alkyl having 1 to 20 carbon atoms•bisphenol A•diphosphite, 4,4'-butylidene-bis(3-methyl-6-t-butylphenyl-di•tridecyl) phosphite. For aromatic organic phosphite, preferably, di, tri, or tetra phosphite derived from aromatic polyhydric alcohol is used, more preferably, tetraphenyl•dipropylene glycol•diphosphite is used.

These organic phosphites may be used singly or in combination of two or more.

For organic phosphites, preferably, alkyl monophosphites, di, tri, or tetra phosphites derived from aromatic polyhydric alcohol, more preferably, tridecylphosphite, tetraphenyl•dipropylene glycol•diphosphite is used.

The mixing ratio of the organic phosphites relative to 100 parts by mass of the 1,3-xylylenediisocyanate is, for example, 0.01 parts by mass (phr) or more, preferably 0.03 parts by mass (phr) or more, and for example, 0.1 parts by mass (phr) or less, preferably 0.07 parts by mass (phr) or less.

By blending the above-described organic phosphite as the promoter at the above-described amount, reaction velocity and reaction rate can be improved, and gellation can be suppressed.

In the above-described reaction, stabilizers including a hindered phenol antioxidant such as 2,6-di(tert-butyl)-4-methylphenol (also called: dibutylhydroxytoluene, hereinafter may be referred to as BHT), IRGANOX 1010, IRGANOX 1076, IRGANOX 1135, and IRGANOX 245 (all manufactured by Ciba Japan K.K., trade name) can be blended.

The mixing ratio of the stabilizer relative to 100 parts by mass of the 1,3-xylylenediisocyanate is, for example, 0.01 parts by mass (phr) or more, preferably 0.02 parts by mass (phr) or more, and for example, 0.05 parts by mass (phr) or less, preferably 0.03 parts by mass (phr) or less.

Furthermore, in the above-described reaction, as necessary, a known reaction solvent can be blended, and furthermore, a known catalyst deactivator (e.g., phosphoric acid, monochloroacetic acid, dodecylbenzenesulfonic acid, p-toluenesulfonic acid, benzoyl chloride, etc.) can be added at arbitrary timing.

Then, after completion of isocyanurate-forming reaction, the unreacted 1,3-xylylenediisocyanate monomer (when reaction solvent and/or catalyst deactivator are blended, reaction solvent and/or catalyst deactivator as well) is removed from the produced reaction mixture liquid of 1,3-xylylenediisocyanate monomer and the isocyanurate composition consisting of an isocyanurate derivative of 1,3-xylylenediisocyanate by a known method such as distillation including thin film distillation (Smith distillation), and extraction. When preparing the mixture liquid of the isocyanurate composition and 1,3-xylylenediisocyanate monomer, without removing the unreacted 1,3-xylylenediisocyanate monomer, the reaction mixture liquid can also be used as a mixture liquid of the isocyanurate composition and 1,3-xylylenediisocyanate monomer as well.

In the present invention, when thin film distillation is performed after completion of isocyanurate-forming reaction of 1,3-xylylenediisocyanate, the isocyanurate composition yield (distillation yield) produced by the thin film distillation is a ratio of a mass of the isocyanurate composition relative to the mass of the reaction mixture liquid, and is, for example, 30 mass % or more, preferably 40 mass % or more, more preferably 55 mass % or more, still more preferably 60 mass % or more, for example, 70 mass % or less, preferably 68 mass % or less, more preferably 64 mass % or less.

The distillation yield of the isocyanurate composition can be obtained in conformity with Examples described later, by calculating the ratio of the mass of the isocyanurate composition relative to the mass of the reaction mixture liquid.

In the above-described reaction, aliphatic alcohol is blended. That is, the isocyanurate composition is modified with aliphatic alcohol.

When the isocyanurate composition is modified with aliphatic alcohol, polyurethane resin (described later) with excellent weatherability (e.g., color difference, gloss retention) and durability (e.g., impact resistance, Erichsen, etc.) can be produced.

In the present invention, for aliphatic alcohol, for example, monohydric aliphatic alcohol, dihydric aliphatic alcohol, trihydric aliphatic alcohol, and aliphatic alcohol having four or more hydrogen atoms are used.

Examples of the monohydric aliphatic alcohol include straight chain monohydric aliphatic alcohol and branched monohydric aliphatic alcohol.

Examples of the straight chain monohydric aliphatic alcohol include methanol, ethanol, n-propanol, n-butanol, n-pentanol, n-hexanol, n-heptanol, n-octanol, n-nonanol, n-decanol, n-undecanol, n-dodecanol (lauryl alcohol), n-tridecanol, n-tetradecanol, n-pentadecanol, n-hexadecanol, n-heptadecanol, n-octadecanol (stearyl alcohol), n-nonadecanol, and eicosanol.

Examples of the branched monohydric aliphatic alcohol include isopropanol (also called: isopropylalcohol, IPA), isobutanol (also called: isobutylalcohol, IBA), sec-butanol, tert-butanol, isopentanol, isohexanol, isoheptanol, isooctanol, 2-ethylhexanol (also called: 2-ethylhexylalcohol, 2-EHA), isononanol, isodecanol, 5-ethyl-2-nonanol, trimethylnonylalcohol, 2-hexyldecanol, 3,9-diethyl-6-tridecanol, 2-isoheptylisoundecanol, 2-octyldodecanol, and other branched alkanol (C (number of carbon, the same applies to the following) 5 to 20).

Examples of the dihydric aliphatic alcohol include straight chain dihydric aliphatic alcohols such as ethylene glycol, 1,3-propanediol (1,3-PG), 1,4-butyleneglycol, 1,5-pentanediol, 1,6-hexanediol, 1,4-dihydroxy-2-butene, diethylene glycol, triethylene glycol, dipropylene glycol, and other straight chain alkane (C7 to 20) diol; branched dihydric aliphatic alcohols such as 1,2-propanediol, 1,3-butyleneglycol (also called: 1,3-butanediol), 1,2-butyleneglycol, neopentyl glycol, 3-methyl-1,5-pentanediol (MPD), 2,2,4-trimethyl-1,3-pentanediol (TMPD), 3,3-dimethylolheptane, 2,6-dimethyl-1-octene-3,8-diol, and other branched alkane (C7 to 20) diol; and alicyclic dihydric aliphatic alcohols such as 1,3- or 1,4-cyclohexanedimethanol, and a mixture thereof, 1,3- or 1,4-cyclohexanediol and a mixture thereof, and hydrogenated bisphenol A.

For the trihydric aliphatic alcohol, for example, glycerin and trimethylolpropane are used.

Examples of the aliphatic alcohol having four or more hydrogen atoms include tetramethylolmethane, D-sorbitol, xylitol, and D-mannitol.

The molecular structure of these aliphatic alcohols is not particularly limited as long as excellent effects of the present invention are not hindered, except that these aliphatic alcohols have one or more hydroxy groups in its molecule and do not include the aromatic ring in its molecule. For example, an ester group, an ether group, and a cyclohexane ring can be contained in its molecule. Examples of the aliphatic alcohol include an ether group-containing monohydric aliphatic alcohol of an addition polymerization product (random and/or block polymer of two or more types of alkyleneoxide) of the above-described monohydric aliphatic alcohol and alkyleneoxide (e.g., ethyleneoxide, propyleneoxide, etc.); and an ester group-containing monohydric aliphatic alcohol of an addition polymerization product of the above-described monohydric aliphatic alcohol and lactone (e.g., ε-polycaprolactone, δ-valerolactone, etc.).

These aliphatic alcohols may be used singly or in combination of two or more.

For the aliphatic alcohol, preferably monohydric and dihydric aliphatic alcohol are used, and more preferably dihydric aliphatic alcohol is used.

Furthermore, for the aliphatic alcohol, preferably, aliphatic alcohol having 1 to 20 carbon atoms, more preferably, aliphatic alcohol having 4 to 20 carbon atoms (aliphatic alcohol having 4 or more and 20 or less carbon atoms), even more preferably, aliphatic alcohol having 4 to 15 carbon atoms is used.

Furthermore, for the aliphatic alcohol, preferably, branched monohydric and dihydric aliphatic alcohol are used, more preferably, branched dihydric aliphatic alcohol is used.

In the present invention, for the aliphatic alcohol, particularly preferably, 1,3-butanediol is used.

The aliphatic alcohol is blended such that the number of the average functional group of the isocyanurate composition is 2 or more, and the mixing ratio of the aliphatic alcohol relative to 100 parts by mass of the 1,3-xylylenediisocyanate is, for example, 0.3 parts by mass or more, preferably 1.0 parts by mass or more, more preferably 1.5 parts by mass or more, and for example, 11 parts by mass or less, preferably 8.0 parts by mass or less, more preferably 7.0 parts by mass or less, still more preferably 5.0 parts by mass or less, particularly preferably 3.0 parts by mass or less.

When the mixing ratio of the aliphatic alcohol is within the above-described range, polyurethane resin (described later) having excellent optical properties, quick-drying properties, weatherability, and durability can be produced.

Furthermore, in this reaction, 1,3-xylylenediisocyanate is blended with aliphatic alcohol with a mixing ratio such that the equivalent ratio (NCO/OH) of the isocyanate group of 1,3-xylylenediisocyanate relative to the hydroxy group of the aliphatic alcohol is, for example, 5 or more, preferably 10 or more, more preferably 20 or more, still more preferably 25 or more, and generally 1000 or less.

In the reaction, within the range that does not hinder excellent effects of the present invention, as necessary, the above-described aliphatic alcohols can be used in combination with an active hydrogen group-containing compound such as, for example, thiols, oximes, lactams, phenols, and β diketones.

The isocyanurate composition can be modified with aliphatic alcohol by, for example, the following methods: first, 1,3-xylylenediisocyanate is allowed to react with aliphatic alcohol, and then after causing isocyanurate-forming reaction in the presence of an isocyanurate-forming catalyst, unreacted 1,3-xylylenediisocyanate is removed; and for example, first, after only 1,3-xylylenediisocyanate is subjected to isocyanurate formation with the above-described method, unreacted 1,3-xylylenediisocyanate is removed, and thereafter, the produced isocyanurate derivative of 1,3-xylylenediisocyanate is allowed to react with aliphatic alcohol.

Preferably, first, 1,3-xylylenediisocyanate is allowed to react with aliphatic alcohol, and then after the isocyanurate-forming reaction is caused in the presence of an isocyanurate-forming catalyst, unreacted 1,3-xylylenediisocyanate (that is, 1,3-xylylenediisocyanate monomer) is removed.

By such a method, that is, allowing 1,3-xylylenediisocyanate to react with aliphatic alcohol and then thereafter subjecting the reaction product to isocyanurate-forming reaction, reaction velocity of the isocyanurate-forming reaction can be improved, and reaction efficiency of the isocyanurate-forming reaction can be improved.

To be specific, in this method, first, 1,3-xylylenediisocyanate is mixed with aliphatic alcohol, and the mixture is allowed to react to obtain a reaction liquid.

The reaction liquid includes 1,3-xylylenediisocyanate, and reaction product (that is, alcohol modified 1,3-xylylenediisocyanate) of 1,3-xylylenediisocyanate and aliphatic alcohol.

The reaction of 1,3-xylylenediisocyanate with aliphatic alcohol is urethane-forming reaction (including allophanate formation reaction), and the reaction conditions are as follows: for example, under an atmosphere of inert gas such as nitrogen gas and normal pressure (atmospheric pressure), reaction temperature of, for example, room temperature (e.g., 25° C.) or more, preferably 40° C. or more, and for example, 100° C. or less, preferably 90° C. or less. The reaction time is, for example, 0.05 hours or more, preferably 0.2 hours or more, and for example, 10 hours or less, preferably 6 hours or less, more preferably 2.5 hours or less.

In the above-described urethane-forming reaction, as necessary, for example, known urethane-forming catalyst such as amines and organometallic compounds can be added at an arbitrary ratio.

Examples of amines include tertiary amines such as triethylamine, triethylenediamine, bis-(2-dimethylaminoethyl) ether, and N-methylmorpholine; quaternary ammonium salts such as tetraethyl hydroxyl ammonium; and imidazoles such as imidazole and 2-ethyl-4-methylimidazole.

Examples of organometallic compounds include organic tin compounds such as tin acetate, stannous octoate, stannous oleate, tin laurate, dibutyl tin diacetate, dimethyl tin dilaurate, dibutyl tin dilaurate, dibutyl tin dimercaptide, dibutyl tin maleate, dibutyl tin dilaurate, dibutyl tin dineodecanoate, dioctyl tin dimercaptide, dioctyl tin dilaurylate, and dibutyl tin dichloride; organic lead compounds such as lead octanoate and lead naphthenate; organic nickel compound such as nickel naphthenate; organic cobalt compounds such as cobalt naphthenate; organic copper compounds such as copper octenate; organic bismuth compounds such as bismuth octylate and bismuth neodecanoate.

Examples of urethane-forming catalysts also include potassium salts such as potassium carbonate, potassium acetate, and potassium octoate.

These urethane-forming catalysts may be used singly or in combination of two or more.

Then, in this method, as described above, the isocyanurate-forming catalyst is blended to the produced reaction liquid, and 1,3-xylylenediisocyanate, and alcohol modified 1,3-xylylenediisocyanate is subjected to isocyanurate-forming reaction. Then, after the completion of the isocyanurate-forming reaction, unreacted 1,3-xylylenediisocyanate monomer is removed, as described above, by a known method.

The aliphatic alcohol modified isocyanurate composition consisting of an isocyanurate derivative of 1,3-xylylenediisocyanate can be produced in this manner.

When, for example, only 1,3-xylylenediisocyanate is subjected to isocyanurate formation and then thereafter, as necessary, unreacted 1,3-xylylenediisocyanate was removed, and the obtained isocyanurate derivative of 1,3-xylylenediisocyanate is allowed to react with aliphatic alcohol (latter method in the above-described method), the isocyanurate derivative of 1,3-xylylenediisocyanate is allowed to react with aliphatic alcohol. This reaction as well is urethane-forming reaction, and the reaction conditions are the same as those in the above-described urethane-forming reaction.

The aliphatic alcohol modified isocyanurate composition consisting of an isocyanurate derivative of 1,3-xylylenediisocyanate can be produced in this manner as well.

With the aliphatic alcohol modified isocyanate composition consisting of an isocyanurate derivative of 1,3-xylylenediisocyanate, polyurethane resin (described later) having excellent optical properties and durability can be produced.

In the following, unless otherwise noted, the isocyanurate derivative of 1,3-xylylenediisocyanate is the isocyanurate derivative of 1,3-xylylenediisocyanate modified with aliphatic alcohol.

The aliphatic alcohol modification amount of the isocyanurate composition (alcohol modification percentage of isocyanurate composition) relative to a total amount of the isocyanurate composition is 0.5 mass % or more, preferably 1.0 mass % or more, more preferably 3.0 mass % or more, and 15 mass % or less, preferably 10 mass % or less, more preferably 7.0 mass % or less, still more preferably 6.0 mass % or less, particularly preferably 5.0 mass % or less, particularly preferably 4.0 mass % or less.

When the aliphatic alcohol modification amount of the isocyanurate composition is within the above-described range, polyurethane resin (described later) having excellent optical properties, quick-drying properties, weatherability, and durability can be produced.

Furthermore, in view of quick-drying properties and weatherability, aliphatic alcohol modification amount of the isocyanurate composition (alcohol modification percentage of isocyanurate composition) relative to a total amount of the isocyanurate composition is preferably 0.5 mass % or more, preferably 7.0 mass % or less, more preferably 6.0 mass % or less, still more preferably less than 5.0 mass %, still more preferably 4.0 mass % or less, still more preferably less than 3.0 mass %, particularly preferably 1.0 mass % or less.

In view of optical properties and durability, aliphatic alcohol modification amount of the isocyanurate composition (alcohol modification percentage of isocyanurate composition) relative to a total amount of the isocyanurate composition is preferably 3.0 mass % or more, more preferably 5.0 mass % or more, still more preferably 10 mass % or more, and preferably 15 mass % or less.

The aliphatic alcohol modification amount of the isocyanurate composition (alcohol modification percentage of isocyanurate composition) can be calculated from the formula below.

Alcohol modification percentage of isocyanurate composition (mass %)=(alcohol modification percentage in reaction mixture liquid (mass %)/distillation yield (mass %))×100

The alcohol modification percentage in reaction mixture liquid is an aliphatic alcohol modification amount of 1,3-xylylenediisocyanate and the isocyanurate composition in the reaction mixture liquid, and can be calculated as a ratio of a charged mass of aliphatic alcohol relative to a charged mass of 1,3-xylylenediisocyanate.

Furthermore, generally, alcohol modification percentage can also be measured with $^1$H-NMR measurement.

For example, in a $^1$H-NMR measurement (400 MHz, solvent CDCL3 (3%), scanning 128 times) of the isocyanurate composition, benzene proton peak of 6.5 to 8.0 ppm is used as the assigned peak of 1,3-xylylenediisocyanate, and methyl proton peak of 0.9 to 1.4 ppm is used as the assigned peak of aliphatic alcohol. Then, their peak area ratio can be calculated as a molar ratio of 1,3-xylylenediisocyanate and aliphatic alcohol. Then, from the calculated molar ratio, a mass ratio of 1,3-xylylenediisocyanate and aliphatic alcohol is calculated, and the alcohol modification percentage can be calculated.

The isocyanurate composition has an isocyanate group concentration (solid content 100 wt %) of, for example, 10.0 mass % or more, preferably 15.0 mass % or more, more preferably 18.0 mass % or more, and for example, 22.0 mass % or less, preferably 21.0 mass % or less, more preferably 20.0 mass % or less, still more preferably 19.0 mass % or less.

The isocyanate group concentration of the isocyanurate composition (solid content 100 wt %) can be determined in conformity with Examples described later.

The isocyanurate composition has an isocyanate monomer concentration (unreacted 1,3-xylylenediisocyanate concentration) of, for example, 2 mass % or less, preferably 1 mass % or less, more preferably 0.5 mass % or less.

In the reaction for producing the isocyanurate composition (urethane-forming reaction and isocyanurate-forming reaction), the isocyanate group conversion rate (reaction rate) is, for example, 20 mass % or more, preferably 30 mass % or more, more preferably 35 mass % or more, and for example, 50 mass % or less, preferably 45 mass % or less, more preferably 40 mass % or less.

Furthermore, in view of improving quick-drying properties and weatherability, in the reaction for producing the isocyanurate composition, the isocyanate group conversion rate (reaction rate) is preferably 20 mass % or more, preferably less than 40 mass %, more preferably 35 mass % or less, still more preferably 33 mass % or less.

Furthermore, in view of improving optical properties and durability, in the reaction for producing the isocyanurate composition, isocyanate group conversion rate (reaction rate) is preferably 40 mass % or more, more preferably 45 mass % or more, and preferably 50 mass % or less.

In the present invention, in the reaction for producing the isocyanurate composition, the isocyanate group conversion rate (reaction rate) is a total value of the urethane conversion rate in the reaction of 1,3-xylylenediisocyanate and aliphatic alcohol, and the isocyanurate conversion rate in the isocyanurate-forming reaction of 1,3-xylylenediisocyanate.

In such a case, the urethane conversion rate is, for example, 0.5 mass % or more, preferably 2.0 mass % or more, more preferably 5.0 mass % or more, and for example, 25 mass % or less, preferably 20 mass % or less, more preferably 10 mass % or less, still more preferably 8.8 mass % or less, 8.0 mass % or less.

The isocyanurate conversion rate is, for example, 15 mass % or more, preferably 25 mass % or more, and for example, 30 mass % or less, preferably 29 mass % or less.

The isocyanate group conversion rate, urethane conversion rate, and isocyanurate conversion rate of 1,3-xylylenediisocyanate are determined by calculating the reduction rate of the isocyanate group concentration of the reaction mixture liquid or reaction liquid relative to the isocyanate group concentration of the charged liquid (including 1,3-xylylenediisocyanate, promoter, stabilizer, and as necessary, reaction solvent) in conformity with Examples described later.

The isocyanurate composition includes isocyanurate derivative not modified with aliphatic alcohol (unmodified isocyanurate derivative) and isocyanurate derivative (alcohol modified isocyanurate derivative) modified with aliphatic alcohol, and preferably, consists of unmodified isocyanurate derivative and alcohol modified isocyanurate derivative.

Examples of the unmodified isocyanurate derivative include a mononuclear isocyanurate (to be specific, a compound in which 3 molecules of 1,3-xylylenediisocyanate form one isocyanurate ring, and the isocyanurate ring is not bonded with other isocyanurate ring, that is, 3 molecules of 1,3-xylylenediisocyanate via one isocyanurate ring) and a polynuclear isocyanurate (e.g., dinuclear isocyanurate (to be specific, a compound in which one mononuclear isocyanurate is bonded with another mononuclear isocyanurate), tri (or more) nuclear isocyanurate (to be specific, a compound in which three or more mononuclear isocyanurates are bonded), etc.).

Examples of the alcohol modified isocyanurate derivative include reaction products of the above-described unmodified isocyanurate derivative and aliphatic alcohol or allophanate derivative (described later).

The isocyanurate composition allows an allophanate derivative to be contained.

Examples of the allophanate derivative include a reaction product of 1,3-xylylenediisocyanate and monohydric aliphatic alcohol (monohydric alcohol modified allophanate derivative), a reaction product of 1,3-xylylenediisocyanate and dihydric aliphatic alcohol (dihydric alcohol modified allophanate derivative), a reaction product of 1,3-xylylenediisocyanate and aliphatic alcohol having three or more hydroxy groups (allophanate derivative modified with alcohol having three or more hydroxyl groups), and furthermore, a reaction product of 1,3-xylylenediisocyanate and the above-described reaction products (monohydric alcohol modified allophanate derivative, dihydric alcohol modified allophanate derivative, or allophanate derivative modified with alcohol having three or more hydroxyl groups).

The monohydric alcohol modified allophanate derivative is, to be specific, a compound in which 1 molecular 1,3-xylylenediisocyanate is allowed to react with monohydric aliphatic alcohol to form urethane bond, and 1 molecular 1,3-xylylenediisocyanate forms allophanate bond to the urethane bond portion.

The dihydric alcohol modified allophanate derivative is, to be specific, a compound in which 2 molecular 1,3-xylylenediisocyanate is bonded through dihydric aliphatic alcohol, and the 1 molecular 1,3-xylylenediisocyanate forms allophanate bond to at least one of the bonded portions (urethane bond), and preferably a compound in which 2 molecular 1,3-xylylenediisocyanate is bonded through the dihydric aliphatic alcohol, and the 1 molecular 1,3-xylylenediisocyanate forms allophanate bond to one of the bonded portions (urethane bond) (trimolecular product of dihydric alcohol modified allophanate derivative).

The allophanate derivative modified with alcohol having three or more hydroxyl groups is in accordance with the above-described dihydric alcohol modified allophanate derivative.

In the chromatogram when the isocyanurate composition is subjected to gel permeation chromatograph measurement, the area percentage (hereinafter trimolecular product area percentage) of a peak area having peak top between the polystyrene-based molecular weight of 400 to 1000, preferably 600 to 900 relative to the total peak area corresponds to a total amount of the mononuclear isocyanurate content and the allophanate derivative content relative to the total amount of the isocyanurate composition, the allophanate derivative being, among the above-described allophanate derivative, the allophanate derivative having a polystyrene-based molecular weight of 400 to 1000, preferably 600 to 900 (preferably trimolecular product of dihydric alcohol modified allophanate derivative), and is, for example, 30% or more, preferably 35% or more, and for example, 51% or less, preferably 45% or less, more preferably 40% or less.

The trimolecular product area percentage can be calculated by measuring the molecular weight distribution of the isocyanurate composition of 1,3-xylylenediisocyanate with a gel permeation chromatograph (GPC) equipped with refractive index detector (RID), as a peak area ratio in the produced chromatogram (chart) in conformity with Examples described later.

To the isocyanurate composition, as necessary, a compound containing a sulfonamide group can be added.

For the compound containing a sulfonamide group, for example, aromatic sulfonamides and aliphatic sulfonamides are used.

Examples of aromatic sulfonamides include benzene sulfonamide, dimethylbenzene sulfonamide, sulfanilamide, o- and p-toluene sulfonamide, hydroxynaphthalene sulfonamide, naphthalene-1-sulfonamide, naphthalene-2-sulfonamide, m-nitrobenzene sulfonamide, and p-chlorobenzene sulfonamide.

Examples of aliphatic sulfonamides include methane sulfonamide, N,N-dimethylmethane sulfonamide, N,N-dimethylethane sulfonamide, N,N-diethylmethane sulfonamide, N-methoxymethane sulfonamide, N-dodecylmethane sulfonamide, N-cyclohexyl-1-butanesulfonamide, and 2-aminoethane sulfonamide.

These compounds containing sulfonamide groups may be used singly or in combination of two or more.

As the compound containing a sulfonamide group, preferably, aromatic sulfonamides are used, more preferably, o- or p-toluene sulfonamides are used.

The compound containing a sulfonamide group is added in an amount relative to 100 parts by mass of the isocyanurate composition of 0.001 to 0.5 parts by mass, preferably 0.005 to 0.4 parts by mass, more preferably 0.01 to 0.3 parts by mass.

When the compound containing a sulfonamide group is added at the above-described amount, improvement in storage stability of the polyisocyanurate composition can be achieved.

The isocyanurate composition does not contain a solvent, but as necessary, by diluting the isocyanurate composition with an organic solvent, the isocyanurate composition can be prepared as a diluted solution of the isocyanurate composition.

Examples of the organic solvent include ketones such as acetone, methyl ethyl ketone, methylisobutylketone, and cyclohexanone; nitriles such as acetinitrile; alkylesters such as methyl acetate, ethyl acetate, butyl acetate, and isobutyl acetate; aliphatic hydrocarbons such as n-hexane, n-heptane, and octane; alicyclic hydrocarbons such as cyclohexane and methylcyclohexane; aromatic hydrocarbons such as toluene, xylene, and ethylbenzene; glycol etheresters such as methylcellosolveacetate, ethylcellosolveacetate, methylcarbitolacetate, ethylcarbitolacetate, ethylene glycolmonoethyletheracetate, propylene glycol monomethyletheracetate, 3-methyl-3-methoxybutylacetate, and ethyl-3-ethoxypropionate; ether such as diethylether, tetrahydrofuran, and dioxane; halogenated aliphatic hydrocarbons such as methyl chloride, methylene chloride, chloroform, carbon tetrachloride, methyl bromide, methylene iodide, and dichloroethane; polar aprotics such as N-methylpyrrolidone, dimethylformamide, N,N'-dimethylacetamide, dimethyl sulfoxide, and hexamethyl phosphor amide.

Examples of organic solvents also include nonpolar solvents (nonpolar organic solvents), and examples of nonpolar solvents include those nonpolar organic solvents having an aniline point of, for example, 10 to 70° C., preferably 12 to 65° C. and having low toxicity and solvency, such as aliphatic, naphthene hydrocarbon organic solvent; and vegetal oils typically represented by turpentine oil.

The nonpolar organic solvents can be obtained from commercially available products, and examples of those commercially available products include petroleum hydrocarbon organic solvents such as Haws (manufactured by Shell Chemicals, aniline point 15° C.), Swasol 310 (manufactured by Maruzen Petrochemical, aniline point 16° C.), Esso Naphtha No. 6 (manufactured by Exxon Mobil Chemical, aniline point 43° C.), Laws (manufactured by Shell Chemicals, aniline point 43° C.), Esso Naphtha No. 5 (manufactured by Exxon Mobil Corporation, aniline point 55° C.), and pegasol 3040 (manufactured by Exxon Mobil Corporation, aniline point 55° C.); and also methylcyclohexane (aniline point 40° C.), ethylcyclohexane (aniline point 44° C.), and turpentine oils such as gum turpentine N (manufactured by YASUHARA CHEMICAL CO., LTD., aniline point 27° C.).

These organic solvents may be used singly or in combination of two or more.

The isocyanurate composition is diluted by mixing the isocyanurate composition with these organic solvents at an arbitrary ratio. The diluted solution of the isocyanurate composition can be prepared in this manner.

When the diluted solution of the isocyanurate composition is prepared, for example, an organic solvent can be blended with the isocyanurate derivative of 1,3-xylylenediisocyanate in advance, or the organic solvent can be blended separately with the isocyanurate composition.

When the diluted solution of the isocyanurate composition is prepared, the isocyanurate composition concentration relative to a total amount of the diluted solution is, for example, 20 mass % or more, preferably 30 mass % or more, and for example, 95 mass % or less, preferably 90 mass % or less.

The diluted solution of the isocyanurate composition has a viscosity at 25° C. (measured with B-type viscometer) of, for example, 10 mPa·s or more, preferably 20 mPa·s or more, and for example, 10000 mPa·s or less, preferably 5000 mPa·s or less.

Such an isocyanurate composition consists essentially of an isocyanurate derivative of 1,3-xylylenediisocyanate, and is an isocyanurate composition in which the above-described isocyanurate derivative is modified with aliphatic alcohol, and the above-described aliphatic alcohol modification amount of the above-described isocyanurate composition is 0.5 mass % or more and 15 mass % or less.

Therefore, with such an isocyanurate composition, polyurethane resin having excellent optical properties, weatherability, quick-drying properties, and durability can be produced.

Therefore, the isocyanurate composition is suitably used in polyurethane resin production.

The isocyanurate composition can be mixed with a monomer and/or derivative of other polyisocyanate, when a polyurethane resin to be described next is produced.

Examples of other polyisocyanate include known or widely used polyisocyanates such as aliphatic polyisocyanate (including alicyclic polyisocyanate), aromatic polyisocyanate, and araliphatic polyisocyanate.

The polyurethane resin can be produced by allowing the polyisocyanate component including the above-described isocyanurate composition with an active hydrogen group-containing compound-containing component.

The polyisocyanate component include the above-described isocyanurate composition, and as necessary, a monomer and/or derivative of the above-described other polyisocyanate.

Examples of the active hydrogen group-containing compound-containing component include polyol components, polythiol components, and polyamine components, and preferably, polyol components are used.

In the present invention, examples of the polyol component include low-molecular-weight polyols and high-molecular-weight polyols.

The low molecular-weight polyol is a compound having two or more hydroxyl groups and a number average molecular weight of generally 40 or more and less than 300, preferably less than 400, and examples thereof include dihydric alcohols such as ethylene glycol, propylene glycol, 1,3-propanediol, 1,4-butyleneglycol, 1,3-butyleneglycol, 1,2-butyleneglycol, 1,5-pentanediol, 1,6-hexanediol, neopentyl glycol, 3-methyl-1,5-pentanediol, 2,2,2-trimethylpentanediol, 3,3-dimethylolheptane, alkane (C 7 to 20) diol, 1,3- or 1,4-cyclohexanedimethanol and a mixture thereof, 1,3- or 1,4-cyclohexanediol and a mixture thereof, hydrogenated bisphenol A, 1,4-dihydroxy-2-butene, 2,6-dimethyl-1-octene-3,8-diol, bisphenol A, diethylene glycol, triethylene glycol, and dipropylene glycol; trihydric alcohols such as glycerin, trimethylolpropane, and triisopropanolamine; tetrahydric alcohols such as tetramethylolmethane (pentaerythritol) and diglycerol; pentahydric alcohols such as xylitol; hexahydric alcohols such as sorbitol, mannitol, allitol, iditol, dulcitol, altritol, inositol, and dipentaerythritol; heptahydric alcohols such as perseitol; and octahydric alcohols such as sucrose.

These low molecular-weight polyols may be used singly or in combination of two or more.

The high molecular weight polyol is a compound having two or more hydroxyl groups and a number average molecular weight of 300 or more, preferably 400 or more, still more preferably 500 or more, and generally 20000 or less, preferably 10000 or less, and examples thereof include polyetherpolyol (e.g., polyoxyalkylenepolyol, polytetramethylene ether polyol, etc.), polyesterpolyol (e.g., adipic acid polyesterpolyol, phthalic acid polyesterpolyol, lactone polyesterpolyol, etc.), polycarbonatepolyol, polyurethane polyol (e.g., polyol produced by subjecting, for example, polyetherpolyol, polyesterpolyol, or polycarbonatepolyol to urethane modification with polyisocyanate), epoxy polyol, vegetable oil polyol, polyolefinpolyol, acrylic polyol, and vinyl monomer-modified polyol.

These high molecular weight polyols may be used singly or in combination of two or more.

For the high molecular weight polyol, acrylic polyol is preferably used.

Then, to produce the polyurethane resin by allowing the above-described polyisocyanate component to react with the above-described active hydrogen group-containing compound-containing component, for example, the polyisocyanate component and the active hydrogen group-containing compound-containing component are blended and polymerized so that the equivalent ratio (NCO/active hydrogen group) of the isocyanate group in the polyisocyanate component relative to the active hydrogen group (e.g., hydroxyl group, mercapto group, amino group, etc.) in the active hydrogen group-containing compound-containing component is, for example, 0.75 to 1.3, preferably 0.9 to 1.1.

For the polymerization method, for example, bulk polymerization and solution polymerization are used.

In the bulk polymerization, for example, the active hydrogen group-containing compound-containing component is added to the polyisocyanate component while stirring under nitrogen flow, and reaction is allowed to occur at a reaction temperature of 50 to 250° C., even more preferably 50 to 200° C., for about 0.5 to 15 hours.

In the solution polymerization, the polyisocyanate component and the active hydrogen group-containing compound-containing component are added to an organic solvent of those organic solvents used for the above-described dilution of the isocyanurate composition, and the mixture is allowed to react at a reaction temperature of 50 to 120° C., preferably 50 to 100° C., for about 0.5 to 15 hours.

Furthermore, in the above-described polymerization reaction, as necessary, the above-described urethane-forming catalyst may be added.

Further, when the above polymerization reaction is more industrially carried out, the polyurethane resin can be produced by a known process such as one shot process and prepolymer process.

In the one shot process, for example, the polyisocyanate component and the active hydrogen group-containing compound-containing component are formulated (mixed) so that the equivalent ratio (NCO/active hydrogen group) of the isocyanate group in the polyisocyanate component relative to the active hydrogen group (e.g., hydroxyl group, mercapto group, amino group, etc.) in the active hydrogen group-containing compound-containing component is, for example, 0.75 to 1.3, preferably 0.9 to 1.1, and thereafter curing reaction is allowed to occur at, for example, room temperature to 250° C., preferably, room temperature to 200° C., for, for example, 5 minutes to 72 hours, preferably 4 to 24 hours. The curing temperature may be a constant temperature, or may be increased/decreased stepwise.

In the prepolymer process, for example, first, the polyisocyanate component is allowed to react with a portion of the active hydrogen group-containing compound-containing component (preferably, high molecular weight polyol) to synthesize an isocyanate group-terminated prepolymer having an isocyanate group at the terminal of the molecule. Then, the produced isocyanate group-terminated prepolymer is allowed to react with the remaining portion of the active hydrogen group-containing compound-containing component (preferably, low molecular-weight polyol and/or polyamine component) to cause chain extension reaction. In the prepolymer process, the remaining portion of the active hydrogen group-containing compound-containing component is used as the chain extender.

To synthesize the isocyanate group-terminated prepolymer, the polyisocyanate component was formulated (mixed) with a portion of the active hydrogen group-containing compound-containing component so that the equivalent ratio (NCO/active hydrogen group) of the isocyanate group in the polyisocyanate component relative to the active hydrogen group in the portion of the active hydrogen group-containing compound-containing component is, for example, 1.1 to 20, preferably 1.3 to 10, still more preferably 1.3 to 6, and the mixture is allowed to react in a reaction vessel at, for example, room temperature to 150° C., preferably 50 to 120° C., for, for example, 0.5 to 18 hours, preferably 2 to 10 hours. In this reaction, as necessary, the above-described urethane-forming catalyst may be added, and after the completion of the reaction, as necessary, the isocyanurate composition and other polyisocyanate in the unreacted polyisocyanate component can be removed, for example, by a known removal method such as distillation and extraction.

Then, to allow the produced isocyanate group-terminated prepolymer to react with the remaining portion of the active hydrogen group-containing compound-containing component, the isocyanate group-terminated prepolymer is formulated (mixed) with the remaining portion of the active hydrogen group-containing compound-containing component so that the equivalent ratio (NCO/active hydrogen group) of the isocyanate group in the isocyanate group-terminated prepolymer relative to the active hydrogen group in the remaining portion of the active hydrogen group-containing compound-containing component is, for example, 0.75 to 1.3, preferably 0.9 to 1.1, and curing reaction is allowed to occur at, for example, room temperature to 250° C., preferably, room temperature to 200° C. for, for example, 5 minutes to 72 hours, preferably 1 to 24 hours.

The polyurethane resin can be produced in this manner.

When the polyurethane resin is produced, as necessary, known additives, for example, a plasticizer, an anti-blocking agent, a heat-resistant stabilizer, a light stabilizer, an antioxidant, a mold release agent, a catalyst, and furthermore a pigment, a dye, a lubricant, a filler, and a hydrolysis prevention agent can be further added at a suitable ratio. These additives may be added at the time of synthesizing components, or may be added at the time of mixing and dissolving components, or may be added after the synthesis.

The polyurethane resin is produced by using the isocyanurate composition of the present invention, and therefore has excellent optical properties, weatherability, quick-drying properties, and durability.

That is, the polyurethane resin produced by using the isocyanurate composition of the present invention has a haze (measured in conformity with Examples described later) of for example, 0.3 or more, and for example, 0.7 or less, preferably 0.6 or less, more preferably 0.4 or less.

The polyurethane resin produced by using the isocyanurate composition of the present invention has a set-to-touch drying time (measured in conformity with Examples described later) of, for example, 100 seconds or more, and for example, 140 seconds or less, preferably 135 seconds or less, more preferably 115 seconds or less, still more preferably 110 seconds or less, particularly preferably 105 seconds or less.

The polyurethane resin produced by using the isocyanurate composition of the present invention has a through-dry time (measured in conformity with Examples described later) of, for example, 95 minutes or more and for example, 125 minutes or less, preferably 120 minutes or less, more preferably 105 minutes or less, still more preferably 100 minutes or less.

The polyurethane resin produced by using the isocyanurate composition of the present invention has a color difference (measured in conformity with Examples described later) of for example, 2.9 or more, and for example, 4.5 or less, preferably 4.3 or less, more preferably 3.8 or less, still more preferably 3.6 or less, still more preferably 3.5 or less, still more preferably 3.4 or less, still more preferably 3.2 or less, particularly preferably 3.1 or less.

The polyurethane resin produced by using the isocyanurate composition of the present invention has a gloss retention (measured in conformity with Examples described later) of, for example, 81% or more, preferably 83% or more, more preferably 85% or more, still more preferably 87% or more, still more preferably 88% or more, still more preferably 90% or more, particularly preferably 91% or more, and for example, 92% or less.

The polyurethane resin produced by using the isocyanurate composition of the present invention has an impact resistance (measured in conformity with Examples described later) of, for example, 40 cm or more, preferably 45 cm or more, and for example, 50 cm or less.

The polyurethane resin produced by using the isocyanurate composition of the present invention has a Erichsen (measured in conformity with Examples described later) of, for example, 7.6 mm or more, preferably 7.7 mm or more, more preferably 7.8 mm or more, still more preferably 8.0 mm or more, particularly preferably 8.1 mm or more, particularly preferably 8.2 mm or less, and for example, 8.3 mm or less.

Therefore, such a polyurethane resin can be widely used in various fields such as, for example, a film coating agent, various inks, adhesives, sealing material, various microcapsules, plastic lens, artificial and synthetic leather, RIM product, slush powder, elastic molded articles (spandex), and urethane foam.

Polyurethane resin (coating resin) produced by using the isocyanurate composition of the present invention can also be produced from a two-component curable polyurethane composition.

The two-component curable polyurethane composition includes a polyisocyanate component prepared as the curing agent, and a polyol component prepared as the main component.

The polyisocyanate component (curing agent) contains the above-described isocyanurate composition of the present invention.

The polyisocyanate component (curing agent) can contain, as necessary, a monomer and/or derivative of the above-described other polyisocyanate and the above-described organic solvent.

When the polyisocyanate component (curing agent) contains an organic solvent, the organic solvent content is not particularly limited, and is set suitably in accordance with the purpose and application.

For the polyol component (main component), the above-described polyol component is used. The polyol component may be used singly or in combination of two or more. For the polyol component, preferably, a high molecular weight polyol is used, even more preferably, acrylic polyol is used.

The polyol component (main component) can contain, as necessary, the above-described organic solvent.

When the polyol component (main component) contains the organic solvent, the organic solvent content is not particularly limited, and is set suitably in accordance with the purpose and application.

In the two-component curable polyurethane composition, the polyisocyanate component (curing agent) is separately prepared from the polyol component (main component), and they are blended and mixed at the time of their use.

The mixing ratio of the polyisocyanate component (curing agent) to the polyol component (main component) is adjusted so that the equivalent ratio (OH/NCO) of the hydroxyl group in the polyol component (main component) relative to the isocyanate group in the polyisocyanate component (curing agent) is, for example, 0.5 or more, preferably 0.75 or more, and for example, 2 or less, preferably 1.5 or less.

To one or both of the polyisocyanate component (curing agent) and the polyol component (main component), as necessary, for example, additives such as epoxy resin, a catalyst, a coating improving agent, a leveling agent, an antifoaming agent, stabilizers including an antioxidant, and an ultraviolet absorber, a plasticizer, a surfactant, a pigment (e.g., titanium oxide), a filler, organic or inorganic microparticles, an antimold agent, and a silane coupling agent can be blended. These additives are blended in an amount suitable for its purpose and use.

The two-component curable polyurethane composition is produced by using the isocyanurate composition of the present invention, and therefore has excellent optical properties, weatherability, and quick-drying properties.

Therefore, the two-component curable polyurethane composition is suitably used in various fields such as paint (plastic paint, automotive paint), adhesives, coating agents, inks, and sealants.

EXAMPLES

In the description below, specific numeral values such as mixing ratios (content), physical property values, and parameters can be replaced with the corresponding upper limit values (numeral values defined with "or less" and "less than") or lower limit values (numeral values defined with "or more" and "more than") of the mixing ratio (content), physical property values, and parameters in the above-described "DESCRIPTION OF EMBODIMENTS".

The measurement methods used in Examples and Comparative Examples are described below.

<Isocyanurate Composition Distillation Yield>

The isocyanurate composition distillation yield was determined by measuring the mass of the reaction mixture liquid (liquid before distillation) and the mass of the isocyanurate composition (liquid after distillation), and by calculating the ratio of the mass of the isocyanurate composition relative to the mass of the reaction mixture liquid based on the following formula.

Isocyanurate composition distillation yield (mass %)=(mass of the isocyanurate composition (g)/mass of the reaction mixture liquid (g))×100

<Aliphatic Alcohol Modification Amount of Isocyanurate Composition (Alcohol Modification Percentage of Isocyanurate Composition)>

The aliphatic alcohol modification amount (alcohol modification percentage in reaction mixture liquid) of the isocyanurate composition and 1,3-xylylenediisocyanate in the reaction mixture liquid was calculated as a charged mass of aliphatic alcohol relative to a charged mass of 1,3-xylylenediisocyanate.

The aliphatic alcohol modification amount of the isocyanurate composition (alcohol modification percentage of isocyanurate composition) was calculated based on the following formula.

Alcohol modification percentage of isocyanurate composition (mass %)=(alcohol modification percentage in reaction mixture liquid (mass %)/distillation yield (mass %))×100

<Isocyanate Group Concentration (Mass %) and Isocyanate Group Conversion Rate (Reaction Rate) Mass %>

The isocyanate group concentration of the charged liquid, reaction liquid, reaction mixture liquid, and the isocyanurate composition was measured in conformity with n-dibutylamine method of JIS K-1556 (2006).

Then, the isocyanate group conversion rate (reaction rate) was determined by calculating the reduction rate of the isocyanate group concentration of the reaction liquid or reaction mixture liquid relative to the isocyanate group concentration of the charged liquid, based on the isocyanate group concentration of the charged liquid, reaction liquid, and reaction mixture liquid.

The urethane conversion rate is the isocyanate group conversion rate (isocyanate group conversion rate of reaction liquid) after blending the aliphatic alcohol and before blending the isocyanurate-forming catalyst, and the isocyanurate conversion rate is the isocyanate group conversion rate (isocyanate group conversion rate of reaction mixture liquid) after blending the isocyanurate-forming catalyst.

<Trimolecular Product Area Percentage>

A sample of the isocyanurate composition was measured with gel permeation chromatography (GPC), and the trimolecular product area percentage was determined from the area percentage of the peak area having peak top between polystyrene-based molecular weight of 400 to 1000 relative to the total peak area in the obtained chromatogram (chart).

The trimolecular product area percentage is the area percentage of a peak area having peak top between the retention time from 26.8 minutes to 27.1 minute relative to the total peak area in the chromatogram (chart) obtained with the device below (ref: FIG. 1).

In the GPC measurement, a sample of about 0.04 g was taken, and subjected to methylurethane formation with methanol, and then thereafter excessive methanol was removed, and 10 mL of tetrahydrofuran was added to dissolve. The prepared solution was subjected to GPC measurement with the following conditions.
(1) Analysis device: Alliance (Waters)
(2) Pump: Alliance 2695 (Waters)
(3) Detector: 2414 type refractive index detector (Waters)
(4) Eluent: Tetrahydrofuran
(5) Separation column: Plgel GUARD+Plgel 5 µm Mixed-C×3 (50×7.5 mm, 300×7.5 mm)
  Manufacturer; Polymer Laboratories
  Product number; PL 1110-6500
(6) Measurement temperature: 40° C.
(7) Flow rate: 1 mL/min
(8) Sample injection amount: 100 µL
(9) Analysis device: EMPOWER data processing device (Waters)
  System Correction
(1) Standard substance name: Polystyrene
(2) Calibration curve making method: using TSK standard Polystyrenes each having a different molecular weight manufactured by TOSOH, a graph for retention time versus molecular weight was made.
(3) Injection amount, injection concentration: 100 µL, 1 mg/mL FIG. 1 shows a gel permeation chromatogram of the isocyanurate composition of Example 4.

<Production of Isocyanurate Composition>

Example 1

A reactor equipped with a thermometer, a stirrer, a nitrogen inlet tube, and a condenser tube was charged with 100 parts by mass of 1,3-xylylenediisocyanate (manufactured by Mitsui Chemicals, Inc., m-XDI), 0.025 phr of 2,6-di (tert-butyl)-4-methylphenol (also called: dibutylhydroxytoluene, BHT, hindered phenol antioxidant), and 0.05 phr of tetraphenyl•dipropylene glycol•diphosphite (JPP-100 (trade name, manufactured by Johoku Chemical Co. Ltd.), organic phosphites, promoter) in a nitrogen atmosphere, and thereafter, to the charged liquid, 0.5 parts by mass of 1,3-butanediol was added, and the temperature of the charged liquid was increased to 75° C., thereby causing urethane-forming reaction. The equivalent ratio (NCO/OH) of the isocyanate group of 1,3-xylylenediisocyanate relative to the hydroxy group of 1,3-butanediol was 96. The liquid charged had an isocyanate group concentration of 44.4 mass %.

Then, after allowing the reaction at the same temperature for 120 minutes, the temperature was reduced to 60° C. At this time, the isocyanate group concentration of the reaction liquid was 44.0 mass %. Then, as an isocyanurate-forming catalyst, 0.008 phr (active component (catalyst) 100% based: 0.003 phr) of 37 mass % methanol solution of hydroxide of tetrabutylammonium (TBAOH) was blended and isocyanurate-forming reaction was caused. Thereafter, during reaction, 0.040 phr (active component (catalyst) 100% based: 0.015 phr) of 37 mass % methanol solution of hydroxide of tetrabutylammonium (TBAOH) was added, and the isocyanurate-forming reaction was terminated at the point when 430 minutes passed from the start of the reaction. The maximum temperature reached during the reaction was 70° C. The isocyanate group concentration of the reaction mixture liquid at this time was 30.9 mass %.

The obtained reaction mixture liquid was passed through a thin film distillation device (temperature 150° C., degree of vacuum 50 Pa), and unreacted 1,3-xylylenediisocyanate was removed, thereby producing an isocyanurate composition consisting of an isocyanurate derivative of 1,3-xylylenediisocyanate. The isocyanurate composition distillation yield was 56.2 mass %.

In this reaction, the aliphatic alcohol modification amount (alcohol modification percentage of isocyanurate composition) of the isocyanurate composition in the reaction mixture liquid (before distillation) was 0.5 mass %, in the isocyanurate composition (after distillation) was 0.89 mass %, and the isocyanate group conversion rate was 30.5 mass %, the urethane conversion rate was 0.9 mass %, and the isocyanurate conversion rate was 29.6 mass %.

The isocyanurate composition had an isocyanate group concentration (solid content 100 wt %) of 20.6 mass %, and the trimolecular product area percentage was 48%.

Examples 2 to 15 and Comparative Examples 1 to 5

The isocyanurate composition consisting of the isocyanurate derivative was produced in the same manner as in Example 1, except that the formulations and production conditions shown in Tables 1 to 4 were used.

The formulation, production conditions, and characteristics of the isocyanurate composition produced in Examples 1 to 15 and Comparative Examples 1 to 5 are shown in Tables 1 to 4.

TABLE 1

| | | | Example No. | | | | |
| --- | --- | --- | --- | --- | --- | --- | --- |
| | | | Example 1 | Example 2 | Example 3 | Example 4 | Example 5 |
| Formulation | Isocyanate | Type | m-XDI | m-XDI | m-XDI | m-XDI | m-XDI |
| | | Parts by mass | 100 | 100 | 100 | 100 | 100 |
| | Aliphatic alcohol | Type | 1,3-BG | 1,3-BG | 1,3-BG | 1,3-BG | 1,3-BG |
| | | Parts by mass | 0.50 | 0.99 | 1.96 | 1.96 | 3.85 |
| | | Equivalent ratio (NCO/OH) | 96 | 48 | 24 | 24 | 12 |
| | Promoter | Type | JPP-100 | JPP-100 | JPP-100 | JPP-100 | JP-310 |
| | | phr | 0.05 | 0.05 | 0.05 | 0.05 | 0.05 |

TABLE 1-continued

|  |  |  | Example 1 | Example 2 | Example 3 | Example 4 | Example 5 |
|---|---|---|---|---|---|---|---|
|  | Antioxidant | Type | BHT | BHT | BHT | BHT | Irg1076 |
|  |  | phr | 0.025 | 0.025 | 0.025 | 0.025 | 0.025 |
|  | Isocyanurate-forming catalyst (active component 100%) | Type | TBAOH | TBAOH | TBAOH | TBAOH | TBAOH |
|  |  | phr (initial period) | 0.003 | 0.003 | 0.003 | 0.003 | 0.003 |
|  |  | phr (additional) | 0.015 | 0.012 | 0.012 | 0.021 | 0.006 |
|  |  | phr (total) | 0.018 | 0.015 | 0.015 | 0.024 | 0.009 |
| Production conditions | Urethane-forming reaction | Reaction temperature (° C.) | 75 | 75 | 75 | 75 | 75 |
|  |  | Reaction time (min) | 120 | 120 | 120 | 120 | 120 |
|  | Isocyanurate-forming reaction | Reaction start temperature (° C.) | 60 | 60 | 60 | 60 | 60 |
|  |  | Highest temperature reached (° C.) | 70 | 70 | 71 | 63 | 74 |
|  |  | Reaction time (min) | 430 | 400 | 390 | 190 | 290 |
| Characteristics | Distillation yield (mass %) |  | 56.2 | 57.5 | 60.0 | 44.7 | 64.8 |
|  | Isocyanate group concentration of liquid charged (mass %) |  | 44.4 | 44.2 | 43.8 | 43.8 | 42.8 |
|  | Isocyanate group concentration of reaction liquid (mass %) |  | 44.0 | 43.3 | 41.4 | 41.3 | 39.0 |
|  | Isocyanate group concentration of reaction mixture liquid (mass %) |  | 30.9 | 30.3 | 28.8 | 33.0 | 26.4 |
|  | Isocyanate group concentration of isocyanurate composition (mass %) |  | 20.6 | 19.9 | 18.8 | 18.7 | 17.3 |
|  | Isocyanate group conversion rate | Conversion rate (total) (mass %) | 30.5 | 31.6 | 34.2 | 24.7 | 38.3 |
|  |  | Urethane conversion rate (mass %) | 0.9 | 2.1 | 5.3 | 5.6 | 8.8 |
|  |  | Isocyanurate conversion rate (mass %) | 29.6 | 29.5 | 28.9 | 19.1 | 29.5 |
|  | Alcohol modification percentage of reaction mixture liquid (mass %) |  | 0.5 | 1.0 | 2.0 | 2.0 | 3.9 |
|  | Alcohol modification percentage of isocyanurate composition (mass %) |  | 0.9 | 1.7 | 3.3 | 4.4 | 5.9 |
|  | Trimolecular product area percentage (%) |  | 48 | 42 | 39 | 51 | 38 |

TABLE 2

|  |  |  | Example 6 | Example 7 | Example 8 | Example 9 | Example 10 |
|---|---|---|---|---|---|---|---|
| Formulation | Isocyanate | Type | m-XDI | m-XDI | m-XDI | m-XDI | m-XDI |
|  |  | Parts by mass | 100 | 100 | 100 | 100 | 100 |
|  | Aliphatic alcohol | Type | 1,3-BG | 1,3-BG | 1,3-BG | 1,3-BG | IBA |
|  |  | Parts by mass | 3.85 | 5.66 | 7.39 | 8.74 | 1.96 |
|  |  | Equivalent ratio (NCO/OH) | 12 | 8 | 6 | 5 | 39 |
|  | Promoter | Type | JP-310 | JP-310 | JP-310 | JP-310 | JPP-100 |
|  |  | phr | 0.05 | 0.05 | 0.05 | 0.05 | 0.05 |
|  | Antioxidant | Type | Irg1076 | Irg1076 | Irg1076 | Irg1076 | BHT |
|  |  | phr | 0.025 | 0.025 | 0.025 | 0.025 | 0.025 |
|  | Isocyanurate-forming catalyst (active component 100%) | Type | TBAOH | TBAOH | TBAOH | TBAOH | TBAOH |
|  |  | phr (initial period) | 0.003 | 0.003 | 0.003 | 0.003 | 0.003 |
|  |  | phr (additional) | 0.006 | 0.006 | 0.006 | 0.006 | 0.012 |
|  |  | phr (total) | 0.009 | 0.009 | 0.009 | 0.009 | 0.015 |
| Production conditions | Urethane-forming reaction | Reaction temperature (° C.) | 75 | 75 | 75 | 75 | 75 |
|  |  | Reaction time (min) | 120 | 120 | 120 | 120 | 120 |
|  | Isocyanurate-forming reaction | Reaction start temperature (° C.) | 60 | 60 | 60 | 60 | 60 |
|  |  | Highest temperature reached (° C.) | 79 | 76 | 78 | 78 | 74 |
|  |  | Reaction time (min) | 200 | 210 | 180 | 160 | 330 |
| Characteristics | Distillation yield (mass %) |  | 59.0 | 68.1 | 68.5 | 68.7 | 59.2 |
|  | Isocyanate group concentration of liquid charged (mass %) |  | 42.8 | 42.0 | 41.4 | 40.6 | 43.8 |
|  | Isocyanate group concentration of reaction liquid (mass %) |  | 38.9 | 36.6 | 34.3 | 32.3 | 42.2 |
|  | Isocyanate group concentration of reaction mixture liquid (mass %) |  | 28.3 | 24.2 | 22.1 | 20.5 | 29.5 |
|  | Isocyanate group concentration of isocyanurate composition (mass %) |  | 18.1 | 15.6 | 13.0 | 10.7 | 19.7 |

TABLE 2-continued

|  |  |  | Example 6 | Example 7 | Example 8 | Example 9 | Example 10 |
|---|---|---|---|---|---|---|---|
| Isocyanate group conversion rate | | Conversion rate (total) (mass %) | 34.0 | 42.4 | 46.5 | 49.6 | 32.6 |
| | | Urethane conversion rate (mass %) | 9.0 | 12.7 | 17.1 | 20.4 | 3.5 |
| | | Isocyanurate conversion rate (mass %) | 25.0 | 29.7 | 29.5 | 29.1 | 29.1 |
| | Alcohol modification percentage of reaction mixture liquid (mass %) | | 3.9 | 5.7 | 7.4 | 8.7 | 2.0 |
| | Alcohol modification percentage of isocyanurate composition (mass %) | | 6.5 | 8.3 | 10.8 | 12.7 | 3.3 |
| | Trimolecular product area percentage (%) | | 40 | 34 | 32 | 31 | 38 |

TABLE 3

|  |  |  | Example 11 | Example 12 | Example 13 | Example 14 | Example 15 |
|---|---|---|---|---|---|---|---|
| Formulation | Isocyanate | Type | m-XDI | m-XDI | m-XDI | m-XDI | m-XDI |
| | | Parts by mass | 100 | 100 | 100 | 100 | 100 |
| | Aliphatic alcohol | Type | 2-EHA | TMPD | MPD | 1,3-PG | IPA |
| | | Parts by mass | 1.96 | 1.96 | 1.96 | 1.96 | 0.50 |
| | | Equivalent ratio (NCO/OH) | 69 | 39 | 31 | 20 | 127 |
| | Promoter | Type | JPP-100 | JPP-100 | JPP-100 | JPP-100 | JPP-100 |
| | | phr | 0.05 | 0.05 | 0.05 | 0.05 | 0.05 |
| | Antioxidant | Type | BHT | BHT | BHT | BHT | BHT |
| | | phr | 0.025 | 0.025 | 0.025 | 0.025 | 0.025 |
| | Isocyanurate-forming catalyst (active component 100%) | Type | TBAOH | TBAOH | TBAOH | TBAOH | TBAOH |
| | | phr (initial period) | 0.003 | 0.003 | 0.003 | 0.003 | 0.003 |
| | | phr (additional) | 0.015 | 0.018 | 0.015 | 0.012 | 0.012 |
| | | phr (total) | 0.018 | 0.021 | 0.018 | 0.015 | 0.015 |
| Production conditions | Urethane-forming reaction | Reaction temperature (° C.) | 75 | 75 | 75 | 75 | 75 |
| | | Reaction time (min) | 120 | 120 | 120 | 120 | 120 |
| | Isocyanurate-forming reaction | Reaction start temperature (° C.) | 60 | 60 | 60 | 60 | 60 |
| | | Highest temperature reached (° C.) | 73 | 72 | 72 | 73 | 69 |
| | | Reaction time (min) | 360 | 360 | 390 | 330 | 420 |
| Characteristics | Distillation yield (mass %) | | 57.8 | 58.9 | 58.4 | 60.9 | 55.7 |
| | Isocyanate group concentration of liquid charged (mass %) | | 43.8 | 43.8 | 43.8 | 43.8 | 44.4 |
| | Isocyanate group concentration of reaction liquid (mass %) | | 42.7 | 42.1 | 41.9 | 41.2 | 44.0 |
| | Isocyanate group concentration of reaction mixture liquid (mass %) | | 29.9 | 29.2 | 29.1 | 28.3 | 30.9 |
| | Isocyanate group concentration of isocyanurate composition (mass %) | | 19.9 | 19.5 | 18.8 | 18.7 | 20.3 |
| | Isocyanate group conversion rate | Conversion rate (total) (mass %) | 31.7 | 33.2 | 33.5 | 35.3 | 30.4 |
| | | Urethane conversion rate (mass %) | 2.4 | 3.8 | 4.3 | 6.0 | 1.0 |
| | | Isocyanurate conversion rate (mass %) | 29.2 | 29.4 | 29.2 | 29.3 | 29.4 |
| | Alcohol modification percentage of reaction mixture liquid (mass %) | | 2.0 | 2.0 | 2.0 | 2.0 | 0.5 |
| | Alcohol modification percentage of isocyanurate composition (mass %) | | 3.4 | 3.3 | 3.4 | 3.2 | 0.9 |
| | Trimolecular product area percentage (%) | | 40 | 41 | 40 | 40 | 46 |

TABLE 4

| | | | Comparative Example No. | | | | |
|---|---|---|---|---|---|---|---|
| | | | Comparative Example 1 | Comparative Example 2 | Comparative Example 3 | Comparative Example 4 | Comparative Example 5 |
| Formulation | Isocyanate | Type | m-XDI | m-XDI | HDI | HDI | m-XDI |
| | | Parts by mass | 100 | 100 | 100 | 100 | 100 |
| | Aliphatic alcohol | Type | 1,3-BG | 1,3-BG | 1,3-BG | 1,3-BG | BA |
| | | Parts by mass | 0.10 | 10.70 | 0.55 | 1.96 | 0.99 |
| | | Equivalent ratio (NCO/OH) | 478 | 4 | 96 | 27 | 115 |
| | Promoter | Type | JPP-100 | JP-310 | JPP-100 | JPP-100 | JPP-100 |
| | | phr | 0.05 | 0.05 | 0.05 | 0.05 | 0.05 |
| | Antioxidant | Type | BHT | Irg1076 | BHT | BHT | BHT |
| | | phr | 0.025 | 0.025 | 0.050 | 0.050 | 0.025 |
| | Isocyanurate-forming catalyst (active component 100%) | Type | TBAOH | TBAOH | DABCO-TMR | DABCO-TMR | TBAOH |
| | | phr (initial period) | 0.003 | 0.003 | 0.005 | 0.005 | 0.003 |
| | | phr (additional) | 0.018 | 0.003 | 0.001 | 0.001 | 0.012 |
| | | phr (total) | 0.021 | 0.006 | 0.006 | 0.006 | 0.015 |
| Production conditions | Urethane-forming reaction | Reaction temperature (° C.) | 75 | 75 | 75 | 75 | 75 |
| | | Reaction time (min) | 120 | 120 | 120 | 180 | 120 |
| | Isocyanurate-forming reaction | Reaction start temperature (° C.) | 60 | 60 | 50 | 50 | 60 |
| | | Highest temperature reached (° C.) | 72 | 79 | 63 | 72 | 70 |
| | | Reaction time (min) | 460 | 140 | 60 | 30 | 330 |
| | | Distillation yield (mass %) | 56.8 | 68.8 | 31.2 | 34.0 | 57.2 |
| Characteristics | | Isocyanate group concentration of liquid charged (mass %) | 44.6 | 39.9 | 49.7 | 49.0 | 43.8 |
| | | Isocyanate group concentration of reaction liquid (mass %) | 44.5 | 29.7 | 49.1 | 47.2 | 42.6 |
| | | Isocyanate group concentration of reaction mixture liquid (mass %) | 31.2 | 18.1 | 41.8 | 40.0 | 29.8 |
| | | Isocyanate group concentration of isocyanurate composition (mass %) | 21.2 | 7.0 | 23.8 | 21.0 | 19.7 |
| | Isocyanate group conversion rate | Conversion rate (total) (mass %) | 30.4 | 54.6 | 15.8 | 18.3 | 32.0 |
| | | Urethane conversion rate (mass %) | 0.3 | 25.6 | 1.1 | 3.7 | 2.7 |
| | | Isocyanurate conversion rate (mass %) | 30.1 | 29.0 | 14.8 | 14.6 | 29.2 |
| | | Alcohol modification percentage of reaction mixture liquid (mass %) | 0.1 | 10.7 | 0.6 | 2.0 | 1.0 |
| | | Alcohol modification percentage of isocyanurate composition (mass %) | 0.2 | 15.6 | 1.8 | 5.8 | 1.7 |
| | | Trimolecular product area percentage (%) | 52 | 29 | 59 | 51 | 43 |

Details of abbreviation in Tables 1 to 4 are shown below.
m-XDI: 1,3-xylylenediisocyanate (manufactured by Mitsui Chemicals, Inc.)
HDI: 1,6-hexamethylene diisocyanate
1,3-BG: 1,3-butanediol
IBA: Isobutylalcohol
2-EHA: 2-ethylhexylalcohol
TMPD: 2,2,4-trimethyl-1,3-pentanediol
MPD: 3-methyl-1,5-pentanediol
1,3-PG: 1,3-propanediol
IPA: Isopropylalcohol
BA: Benzylalcohol
JPP-100: Tetraphenyl•dipropylene glycol•diphosphite (aromatic organic phosphite, manufactured by Johoku Chemical Co. Ltd., trade name)
JP-310: tridecyl phosphite (aliphatic organic phosphite, manufactured by Johoku Chemical Co. Ltd., trade name)
BHT: 2,6-di (tert-butyl)-4-methylphenol (hindered phenol antioxidant)
Irg1076: IRGANOX 1076 (hindered phenol antioxidant, manufactured by Ciba Japan K.K., trade name)
TBAOH: 37 mass % methanol solution of hydroxide of tetrabutylammonium
DABCO-TMR: N-(2-hydroxypropyl)-N,N,N-trimethylammonium-2-ethylhexanoate, manufactured by Air Products and Chemicals, Inc.

Comparative Example 6

Commercially available trimethylolpropane modified xylylenediisocyanate (trade name: D-110N, NCO group content: 11.5 wt %, solid content 75 wt %, solvent: ethyl acetate, viscosity (25° C.): 500 mPa·s, manufactured by Mitsui Chemicals, Inc.) was used as is.

Comparative Example 7

Commercially available isocyanurate derivative of 1,6-hexamethylene diisocyanate (trade name: D-170N, NCO group content: 20.7 wt %, solid content 100 wt %, viscosity (25° C.): 200 mPa·s, manufactured by Mitsui Chemicals, Inc.) was used as is.

Comparative Example 8

Commercially available isocyanurate derivative of bis (isocyanatomethyl) cyclohexane (trade name: D-127N, NCO group content: 13.5 wt %, solid content 75 wt %, solvent: ethyl acetate, viscosity (25° C.): 40 mPa·s, manufactured by Mitsui Chemicals, Inc.) was used as is.

Tables 5 and 6 show types of the aliphatic alcohol used for production of the isocyanurate composition of Examples 1 to 15 and Comparative Examples 1 to 8 and the alcohol modification percentage of isocyanurate composition of Examples 1 to 15 and Comparative Examples 1 to 8. The types of the aliphatic alcohol of Comparative Examples 6 to 8 and the alcohol modification percentage of isocyanurate composition of Comparative Examples 6 to 8 are not shown.
<Evaluation>
(Measurement of Aliphatic Alcohol Modification Amount (Alcohol Modification Percentage of Isocyanurate Composition) of the Isocyanurate Composition of 1,3-Xylylenediisocyanate)

In the isocyanurate composition produced in Example 4, comparison was made between the aliphatic alcohol (1,3-butanediol) modification amount (alcohol modification percentage of isocyanurate composition) of the isocyanurate composition calculated from the charged amount and the aliphatic alcohol (1,3-butanediol) modification amount (alcohol modification percentage of isocyanurate composition) of the isocyanurate composition calculated by $^1$H-NMR.
[Calculation of the Alcohol Modification Percentage of Isocyanurate Composition from Charged Amount]

The values are put into the above-described formulas shown in the method for determining the aliphatic alcohol modification amount of the isocyanurate composition, and the 1,3-butanediol modification amount (alcohol modification percentage of isocyanurate composition) of the isocyanurate composition in the isocyanurate composition of Example 4 was determined to be, as shown in the formula below, 4.4 mass %.

1.96 (alcohol modification percentage in the reaction mixture liquid calculated from the charged mass)/44.7 (distillation yield))×100=4.4 (mass %)

[Calculation of the Alcohol Modification Percentage of Isocyanurate Composition by $^1$H-NMR]

A $^1$H-NMR measurement (400 MHz, solvent CDCL3 (3%), scanning 128 times) was conducted for the isocyanurate composition of Example 4, and the benzeneproton peak of 6.5 to 8.0 ppm was regarded as the assigned peak of 1,3-xylylenediisocyanate, and the methylproton peak of 0.9 to 1.4 ppm was regarded as the assigned peak of 1,3-butanediol. Then, the molar ratio of 1,3-xylylenediisocyanate and 1,3-butanediol was calculated from their peak area ratios. Then, from the calculated molar ratio, the mass ratio of 1,3-xylylenediisocyanate and 1,3-butanediol was calculated, and the alcohol modification percentage of the isocyanurate composition of Example 4 was calculated.

Figure 2:
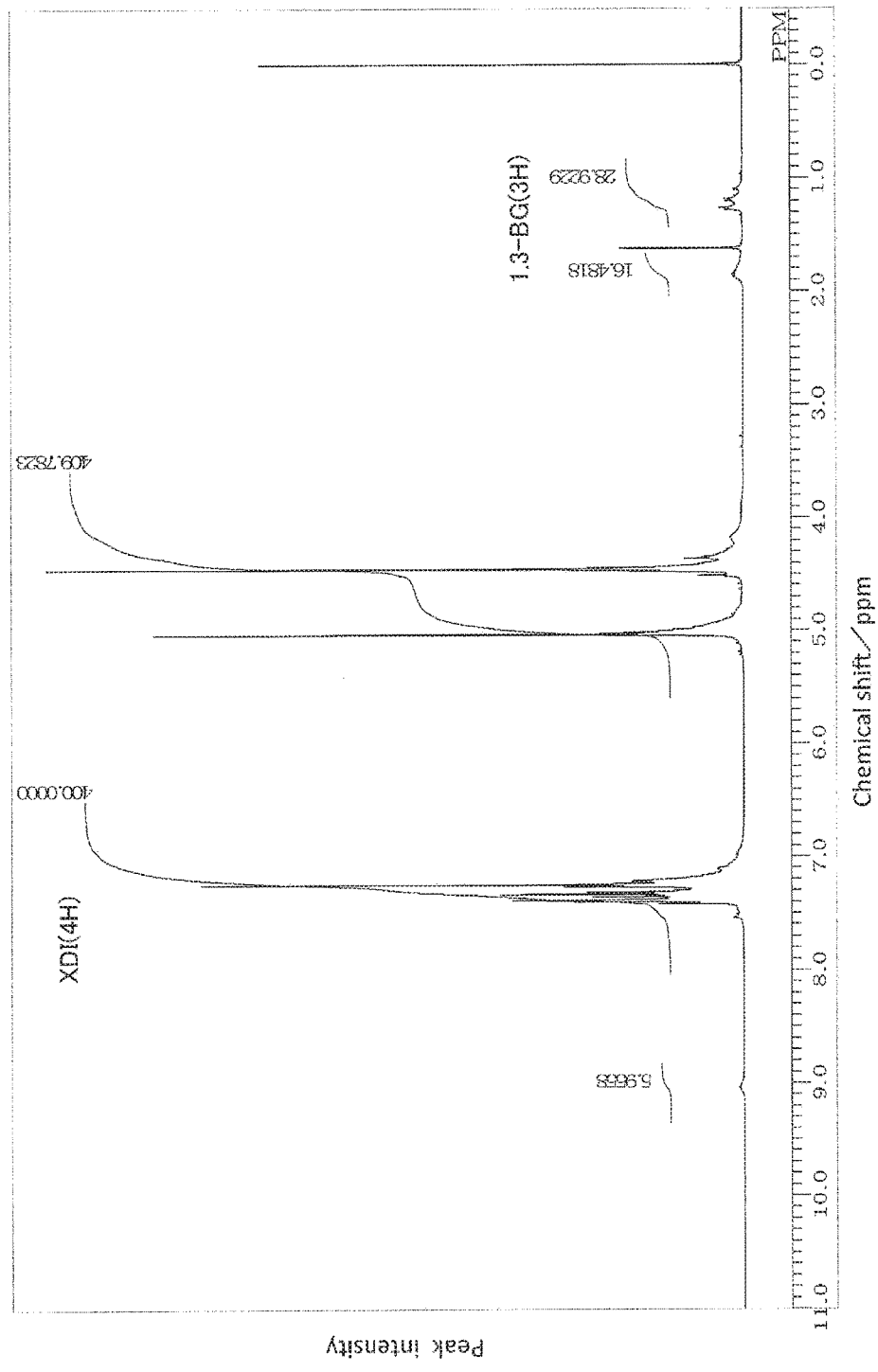
FIG. 2 is a $^1$H-NMR chart of the isocyanurate composition of Example 4.

The $^1$H-NMR chart of the isocyanurate composition of Example 4 is shown in FIG. 2.

In the $^1$H-NMR chart, the area ratio of benzeneproton assigned peak (4H) of 1,3-xylylenediisocyanate to methylproton assigned peak (3H) of 1,3-butanediol was benzeneproton assigned peak of 1,3-xylylenediisocyanate:methylproton assigned peak (3H) of 1,3-butanediol=400.0000: 28.9229.

Therefore, the molar ratio of 1,3-xylylenediisocyanate to 1,3-butanediol was 1,3-xylylenediisocyanate:1,3-butanediol=400.0000/4:28.9229/3=100:9.64.

Therefore, when the molecular weight of 1,3-xylylenediisocyanate was 188.2, and when the molecular weight of 1,3-butanediol was 90.1, in the isocyanurate composition of Example 4, the 1,3-butanediol modification amount (alcohol modification percentage of isocyanurate composition) of the isocyanurate composition was, based on the calculation below, 4.4 mass %.

(9.64 (molar amount of 1,3-butanediol)×90.1)/(100 (molar amount of 1,3-xylylenediisocyanate)× 188.2+9.64 (molar amount of 1,3-butanediol)× 90.1)×100=4.4 (mass %)

Based on the above, the same values were obtained for the alcohol modification percentage when the alcohol modification percentage of isocyanurate composition was calculated from the ratio of the charged mass of aliphatic alcohol relative to the charged mass of 1,3-xylylenediisocyanate, and the alcohol modification percentage of isocyanurate composition was calculated by $^1$H-NMR chart of the isocyanurate composition.

From the above, it was confirmed that the alcohol modification percentage of isocyanurate composition could be calculated from the charged amounts of the 1,3-xylylenediisocyanate and aliphatic alcohol.
(Preparation of Coating Solution)

The isocyanurate composition produced in Examples and Comparative Examples was blended with acrylic polyol (manufactured by Mitsui Chemicals, Inc., trade name: OLESTERQ666, hereinafter abbreviated as Q666) so that the equivalent ratio (NCO/OH) of the hydroxyl group in the acrylic polyol relative to the isocyanate group in the isocyanurate composition was 1.0, and the mixture was diluted with a thinner (1:1:1 weight ratio mixture of ethyl acetate/propylene glycol monomethyletheracetate/butyl acetate) so that the solid content was 50 mass %. Thereafter, the mixture was stirred at 23° C. for 5 minutes. Furthermore, ultrasonic treatment was conducted for 10 minutes for defoaming, thereby producing a coating solution.
(Production of Urethane Film)

The coating solution produced by the above-described method was applied on a steel plate (SPCC, PBN-144 treated) and on a polymethyl methacrylate (PMMA) plate so that the dried film had a thickness of 40 μm, and on a glass plate so that the dried film had a thickness of 100 μm. Then, after drying at 23° C. for 2 hours, they were heated at 80° C. for 30 minutes. Thereafter, they were aged at 23° C. and a relative humidity of 55% for 7 days, thereby producing a urethane film on the steel plate, PMMA plate, and glass plate.

The produced films were used for physical property evaluation below.
<Physical Property Evaluation>
(Set to Touch Drying Time)

The coating solution was applied using an applicator so that the thickness (thickness before drying) was 100 μm on the glass plate. After the application, the time until there is no tack when touched with a finger was measured at 23° C. and under a relative humidity of 30%.
(Through-dry Time)

The coating solution was applied using an applicator so that the thickness (thickness before drying) was 100 μm on the glass plate. After the application, the time was measured until there is no fingerprint mark when a finger is pressed strongly at 23° C. and a relative humidity of 30%.
(Evaluation of Compatibility of Film Form)

The haze of the urethane film applied on the glass plate was evaluated with a haze meter (manufactured by Nippon Denshoku Industries Co., Ltd., NDH2000).
(Evaluation on Weatherability)

With a super accelerated weathering test instrument (Dewpanel Light Control Weather Meter, manufactured by Suga Test Instruments Co., Ltd.), the urethane film applied on the PMMA plate was treated with cycles of daytime (60° C.×relative humidity 10%×4 hours×light irradiation), and night time (50° C.×relative humidity 95%×4 hours×no light irradiation) for 600 hours. The urethane film before and after the treatment was evaluated with a color difference meter (Manufactured by Nippon Denshoku Industries Co., Ltd., SE2000), and the color difference (ΔE) before and after the treatment was calculated. Gross was evaluated by a gross meter (manufactured by Nippon Denshoku Industries Co., Ltd., VG2000), and gloss retention (after 600 hours) setting the initial gross as 100 was calculated.

(Evaluation of Impact Resistance (DuPont Impact))

The urethane film applied on the steel plate was sandwiched between the ½ inch impact head and receive block of the DuPont impact tester, and using a weight (300 g), impact was applied on the face (surface) where the urethane film was formed of the steel plate, and the height (cm) when damage was caused on the urethane film was measured.

(Evaluation of Erichsen Test)

In conformity with JIS K 5600-5-2 (1999), a 20 mm diameter drawing punch was applied on a side of the steel plate opposite to the side where urethane film was applied, and while firmly fixing the steel plate, the drawing punch was pushed at a predetermined speed, and the pushed length at which cracks and peelings were caused on the urethane film surface were evaluated as Erichsen (mm).

Table 5 and Table 6 show the evaluations for Examples and Comparative Examples. The impact resistance and Erichsen for Comparative Examples 8 and 9 are not shown because there were not measured.

TABLE 5

|  |  | Example No. | | | | |
| --- | --- | --- | --- | --- | --- | --- |
|  |  | Example 1 | Example 2 | Example 3 | Example 4 | Example 5 |
|  | Aliphatic alcohol Type | 1,3-BG | 1,3-BG | 1,3-BG | 1,3-BG | 1,3-BG |
|  | Alcohol modification percentage of isocyanurate composition (mass %) | 0.9 | 1.7 | 3.3 | 4.4 | 5.9 |
| Evaluation | Haze | 0.6 | 0.4 | 0.4 | 0.4 | 0.4 |
|  | Set to touch drying time (sec) | 100 | 100 | 100 | 105 | 105 |
|  | Through-dry time (min) | 95 | 95 | 95 | 100 | 100 |
|  | Color difference ΔE | 2.9 | 3.1 | 3.1 | 3.5 | 3.5 |
|  | Gloss retention (%) | 91 | 92 | 92 | 92 | 92 |
|  | Impact resistance (cm) | 45 | 45 | 50 | 50 | 50 |
|  | Erichsen (mm) | 7.6 | 7.8 | 8.1 | 8.1 | 8.2 |

|  |  | Example No. | | | | |
| --- | --- | --- | --- | --- | --- | --- |
|  |  | Example 6 | Example 7 | Example 8 | Example 9 | Example 10 |
|  | Aliphatic alcohol Type | 1,3-BG | 1,3-BG | 1,3-BG | 1,3-BG | IBA |
|  | Alcohol modification percentage of isocyanurate composition (mass %) | 6.5 | 8.3 | 10.8 | 12.7 | 3.3 |
| Evaluation | Haze | 0.4 | 0.4 | 0.3 | 0.3 | 0.4 |
|  | Set to touch drying time (sec) | 115 | 135 | 135 | 140 | 110 |
|  | Through-dry time (min) | 105 | 120 | 125 | 125 | 105 |
|  | Color difference ΔE | 3.6 | 4.3 | 4.4 | 4.5 | 3.7 |
|  | Gloss retention (%) | 90 | 85 | 83 | 82 | 87 |
|  | Impact resistance (cm) | 50 | 50 | 50 | 50 | 50 |
|  | Erichsen (mm) | 8.2 | 8.3 | 8.3 | 8.3 | 8.0 |

|  |  | Example No. | | | | |
| --- | --- | --- | --- | --- | --- | --- |
|  |  | Example 11 | Example 12 | Example 13 | Example 14 | Example 15 |
|  | Aliphatic alcohol Type | 2-EHA | TMPD | MPD | 1,3-PG | IPA |
|  | Alcohol modification percentage of isocyanurate composition (mass %) | 3.4 | 3.3 | 3.4 | 3.2 | 0.9 |
| Evaluation | Haze | 0.4 | 0.4 | 0.4 | 0.4 | 0.4 |
|  | Set to touch drying time (sec) | 110 | 110 | 110 | 110 | 115 |
|  | Through-dry time (min) | 105 | 100 | 100 | 105 | 105 |
|  | Color difference ΔE | 3.7 | 3.4 | 3.4 | 3.5 | 3.8 |
|  | Gloss retention (%) | 88 | 90 | 90 | 83 | 81 |
|  | Impact resistance (cm) | 50 | 45 | 45 | 45 | 45 |
|  | Erichsen (mm) | 8.1 | 7.7 | 7.7 | 7.6 | 7.6 |

TABLE 6

|  | Comparative Example No. | | | |
|---|---|---|---|---|
|  | Comparative Example 1 | Comparative Example 2 | Comparative Example 3 | Comparative Example 4 |
| Aliphatic alcohol Type | 1,3-BG | 1,3-BG | 1,3-BG | 1,3-BG |
| Alcohol modification percentage of isocyanurate composition (mass %) | 0.2 | 15.6 | 1.8 | 5.8 |
| Evaluation Haze | 0.7 | 0.3 | 0.3 | 0.4 |
| Set to touch drying time (sec) | 100 | 170 | 180 | 190 |
| Through-dry time (min) | 95 | 155 | 155 | 160 |
| Color difference ΔE | 2.8 | 6.3 | 1.6 | 1.9 |
| Gloss retention (%) | 91 | 62 | 100 | 99 |
| Impact resistance (cm) | 30 | 50 | 50 | 50 |
| Erichsen (mm) | 6.6 | 8.2 | 8.1 | 8.2 |

|  | Comparative Example No. | | | |
|---|---|---|---|---|
|  | Comparative Example 5 | Comparative Example 6 | Comparative Example 7 | Comparative Example 8 |
| Aliphatic alcohol Type | BA | — | — | — |
| Alcohol modification percentage of isocyanurate composition (mass %) | 1.7 | — | — | — |
| Evaluation Haze | 0.4 | 0.4 | 0.4 | 0.4 |
| Set to touch drying time (sec) | 105 | 120 | 150 | 170 |
| Through-dry time (min) | 100 | 105 | 140 | 140 |
| Color difference ΔE | 5.2 | 6.7 | 1.8 | 2.1 |
| Gloss retention (%) | 55 | 51 | 99 | 99 |
| Impact resistance (cm) | 40 | 50 | — | — |
| Erichsen (mm) | 7.2 | 8.3 | — | — |

Details of abbreviation in Tables 5 and 6 are shown below (those abbreviations described for the above-described Tables 1 to 4 are omitted.).

D-110N: trimethylolpropane modified xylylenediisocyanate (NCO group content: 11.5 wt %, solid content 75 wt %, solvent: ethyl acetate, viscosity (25° C.): 500 mPa·s, manufactured by Mitsui Chemicals. Inc.)

D-170N: isocyanurate derivative of 1,6-hexamethylene diisocyanate (NCO group content: 20.7 wt %, solid content 100 wt %, viscosity (25° C.): 200 mPa·s, manufactured by Mitsui Chemicals, Inc.)

D-127N: isocyanurate derivative of bis(isocyanatomethyl) cyclohexane (NCO group content: 13.5 wt %, solid content 75 wt %, solvent: ethyl acetate, viscosity (25° C.): 40 mPa·s, manufactured by Mitsui Chemicals, Inc.)

While the illustrative embodiments of the present invention are provided in the above description, such is for illustrative purpose only and it is not to be construed as limiting in any manner. Modification and variation of the present invention that will be obvious to those skilled in the art is to be covered by the following claims.

INDUSTRIAL APPLICABILITY

The isocyanurate composition of the present invention is useful as a material of polyurethane resin, and the polyurethane resin produced from the isocyanurate composition of the present invention can be used in a wide range in various industrial fields.

The invention claimed is:

1. An isocyanurate composition consisting essentially of an isocyanurate derivative of 1,3-xylylenediisocyanate,
    wherein the isocyanurate derivative includes a trimer of 1,3-xylylenediisocyanate,
    the isocyanurate derivative is modified with aliphatic alcohol, and
    the modification amount of the aliphatic alcohol is 0.5 mass % or more and 15 mass % or less.

2. The isocyanurate composition according to claim 1, wherein the modification amount of the aliphatic alcohol is 3.0 mass % or more and 7.0 mass % or less.

3. The isocyanurate composition according to claim 1, wherein the aliphatic alcohol has carbon atoms of 4 or more and 20 or less.

4. The isocyanurate composition according to claim 1, wherein the aliphatic alcohol is dihydric aliphatic alcohol.

5. An isocyanurate composition consisting essentially of an isocyanurate and an aliphatic alcohol-modified isocyanurate,
    wherein the isocyanurate is at least one selected from a group consisting of a mononuclear isocyanurate which is a trimer of 1,3-xylylenediisocyanate and a polynuclear isocyanurate of two or more of the mononuclear isocyanurates, and
    the modification amount of the aliphatic alcohol is 0.5 mass % or more and 15 mass % or less relative to a total amount of the isocyanurate composition.

* * * * *